United States Patent
Wilson et al.

(10) Patent No.: US 10,930,391 B2
(45) Date of Patent: Feb. 23, 2021

(54) DEVICE FOR REDUCING FRAUD, WASTE, AND ABUSE IN THE ORDERING AND PERFORMANCE OF MEDICAL TESTING AND METHODS FOR USING THE SAME

(71) Applicant: Optum, Inc., Minnetonka, MN (US)

(72) Inventors: John L. Wilson, Scottsdale, AZ (US); François Charette, Edina, MN (US)

(73) Assignee: Optum, Inc., Minnetonka, MN (US)

(*) Notice: Subject to any disclaimer, the term of this patent is extended or adjusted under 35 U.S.C. 154(b) by 107 days.

(21) Appl. No.: 15/888,721

(22) Filed: Feb. 5, 2018

(65) Prior Publication Data
US 2019/0244706 A1 Aug. 8, 2019

(51) Int. Cl.
*G16H 40/20* (2018.01)
*G16H 10/40* (2018.01)
*G16H 10/60* (2018.01)
*G16H 70/20* (2018.01)

(52) U.S. Cl.
CPC ............. *G16H 40/20* (2018.01); *G16H 10/40* (2018.01); *G16H 10/60* (2018.01); *G16H 70/20* (2018.01)

(58) Field of Classification Search
CPC .................................................. G06Q 50/22–24
See application file for complete search history.

(56) References Cited

U.S. PATENT DOCUMENTS

| | | | |
|---|---|---|---|
| 6,306,087 B1 | 10/2001 | Barnhill et al. | |
| 6,343,271 B1 | 1/2002 | Peterson et al. | |
| 6,879,959 B1 | 4/2005 | Chapman et al. | |
| 8,229,759 B2 | 7/2012 | Zhu et al. | |
| 8,731,966 B2 | 5/2014 | Breitenstein et al. | |
| 9,779,129 B1* | 10/2017 | Lequeux | G06F 16/24 |
| 2002/0016923 A1 | 2/2002 | Knaus et al. | |
| 2003/0229519 A1* | 12/2003 | Eidex | G16H 50/20 |
| | | | 705/2 |
| 2004/0117205 A1* | 6/2004 | Reardan | G16H 20/10 |
| | | | 705/2 |
| 2004/0225282 A1 | 11/2004 | Ness | |
| 2006/0190295 A1* | 8/2006 | Merkin | G16H 15/00 |
| | | | 705/2 |
| 2007/0294103 A1 | 12/2007 | Ahmad et al. | |
| 2008/0033751 A1* | 2/2008 | Greene | G06Q 40/04 |
| | | | 705/2 |
| 2008/0120133 A1 | 5/2008 | Krishnaswami et al. | |
| 2008/0147436 A1 | 6/2008 | Ohlsson | |
| 2008/0288407 A1* | 11/2008 | Hamel | G06Q 10/10 |
| | | | 705/50 |
| 2009/0006135 A1 | 1/2009 | Keck et al. | |

(Continued)

OTHER PUBLICATIONS

International Search Report and Written Opinion for corresponding International Application No. PCT/US2018/016901, dated Jun. 11, 2018, 13 pages.

(Continued)

*Primary Examiner* — Neal Sereboff
(74) *Attorney, Agent, or Firm* — Alston & Bird LLP

(57) ABSTRACT

Provided is a lab clearinghouse device configured to reduce fraud, waste, and abuse in the ordering and performance of medical testing. The lab clearinghouse device is configured to communicate with a plurality of medical laboratories, medical providers, and lab payers to efficiently and effectively reduce fraud, waste, and abuse in the ordering and performance of medical testing.

16 Claims, 8 Drawing Sheets

(56) References Cited

U.S. PATENT DOCUMENTS

| | | | |
|---|---|---|---|
| 2009/0222283 A1 | 9/2009 | Lassetter et al. | |
| 2010/0274723 A1* | 10/2010 | Joao | G06Q 20/4016 705/44 |
| 2011/0202370 A1 | 8/2011 | Green et al. | |
| 2012/0029933 A1 | 2/2012 | Zubiller et al. | |
| 2013/0110755 A1 | 5/2013 | Upadhyayula et al. | |
| 2013/0173278 A1 | 7/2013 | Owings et al. | |
| 2013/0173289 A1 | 7/2013 | Owings et al. | |
| 2013/0173290 A1 | 7/2013 | Owings et al. | |
| 2014/0012599 A1 | 1/2014 | Weiss | |
| 2014/0222456 A1* | 8/2014 | Abou Nader | G16H 20/10 705/2 |
| 2014/0379361 A1* | 12/2014 | Mahadkar | G06Q 10/10 705/2 |
| 2015/0046181 A1* | 2/2015 | Adjaoute | G06N 5/04 705/2 |
| 2015/0081324 A1* | 3/2015 | Adjaoute | G06Q 40/08 705/2 |
| 2015/0235334 A1 | 8/2015 | Wang et al. | |
| 2015/0278743 A1* | 10/2015 | Callas | G06Q 10/10 705/2 |
| 2015/0371001 A1 | 12/2015 | Pinsonneault et al. | |
| 2016/0000515 A1 | 1/2016 | Sela et al. | |
| 2016/0110512 A1* | 4/2016 | Adjaoute | G06Q 10/10 705/2 |
| 2016/0321406 A1 | 11/2016 | Timmerman et al. | |
| 2016/0321410 A1 | 11/2016 | Timmerman et al. | |
| 2016/0350498 A1 | 12/2016 | Hashoul et al. | |
| 2017/0124263 A1 | 5/2017 | Crafts, Jr. et al. | |
| 2017/0286622 A1* | 10/2017 | Cox | G06F 19/00 |
| 2018/0011980 A1 | 1/2018 | Contu et al. | |
| 2018/0089781 A1 | 3/2018 | Landrum et al. | |
| 2018/0096292 A1* | 4/2018 | DeBusk | G16H 10/60 |
| 2018/0204111 A1* | 7/2018 | Zadeh | G06K 9/3233 |

OTHER PUBLICATIONS

United States Patent and Trademark Office, NonFinal Office Action for U.S. Appl. No. 15/888,682, dated Nov. 27, 2019, (23 pages), USA.

United States Patent and Trademark Office, NonFinal Office Action for U.S. Appl. No. 15/888,763, dated Nov. 20, 2019, (33 pages), USA.

U.S. Patent and Trademark Office, Final Office Action for U.S. Appl. No. 15/888,763, dated Mar. 25, 2020, (22 pages), USA.

Office Action for U.S. Appl. No. 15/888,763 dated Nov. 20, 2019. Spend more time on care, less on billing claims and reimbursements (2017 copyright), NextGen, NextGen Clearinghouse, 6 pages, https://www.nextgen.com/eServices/Clearinghouse, Aug. 18, 2017.

Reduction in Unnecessary Clinical Laboratory Testing Through Utilization Management at a US Government Veteran Affairs Hospital, Electronic Lab Utilization Management, Mar. 1, 2016, Konger, R. L., et al., American Journal of Pathology, pp. 355-364, 145.

Provider Payment Arrangements, Provider Risk, and Their Relationship with the Cost of Health Care, Oct. 1, 2015, Spector, Juliet M., et al., Society of Actuaries (Milliman), 91 pages.

Preventing Duplicate Laboratory Testing, May 9, 2015, Tim H, Physician's Weekly for Medical News, Journals & Articles, 4 pages, http://www.physiciansweekly.com/preventing-duplicate-laboratory-testing/, Aug. 17, 2017.

Mirth Results. Powering Health Information Exchange. (2017 Copyright), NextGen, NextGen Mirth, 4 pages, https://www.nextgen.com/Interoperability/Mirth-Solutions, Aug. 18, 2017.

ISA/206—Invitation to Pay Additional Fees dated Apr. 12, 2018 for WO Application No. PCT/US18/016901.

IBM Counter Fraud on Cloud, (Unknown Author), 3 pages, https://www.ibm.com/bs-en/marketplace/financial-risk-and-fraud, Aug. 18, 2017.

Data Science Labs: Predictive Modeling to Detect Healthcare Fraud, Waste, and Abuse, May 9, 2013, Noah Zimmerman, Pivotal Blog, 5 pages, https://network.pivotal.io.

Contingent Payment Clauses: Enforceable? Negotiable? Worth the Risk?, Jan. 1, 2015, Matt Meaker, SacksTierney P.A., 3 pages, http://www.sackstierney.com/articles/contingent-payment-clauses.htm, Aug. 18, 2017.

United States Patent and Trademark Office, Final Office Action for U.S. Appl. No. 15/888,682, dated May 14, 2020, (18 pages), USA.

* cited by examiner

DEVICE FOR REDUCING FRAUD, WASTE, AND ABUSE IN THE ORDERING AND PERFORMANCE OF MEDICAL TESTING AND METHODS FOR USING THE SAME

BACKGROUND

Laboratory medicine involves the process of capturing specimens and performing tests on the specimens. Applicant has identified a number of deficiencies and problems associated with conventional processing of medical laboratory orders and results. Through applied effort, ingenuity, and innovation, many of these identified problems have been solved by developing solutions that are included in embodiments of the present invention, many examples of which are described in detail herein.

BRIEF SUMMARY

In general, embodiments of the present invention provided herein include methods, devices, and computer program products for facilitating laboratory medicine processing.

In a first embodiment, a device is provided for reducing fraud, waste, and abuse in the ordering and performance of medical tests across a plurality of medical laboratories, medical providers, and lab payers, the device including a processor and a memory storing computer instructions that, when executed by the processor, cause the device to receive a lab request from a lab request initiator. The lab request initiator may be associated with at least one medical provider of the plurality of medical providers and the lab request may include an order for one or more medical tests to be performed. The computer instructions, when executed by the processor, may cause the device to determine whether at least one of fraud, waste, or abuse in the lab request is likely by determining whether the lab request aligns with pre-established data associated with the lab request. The pre-established data associated with the lab request may include patient data, physician data, provider data, lab data, payer data, or a combination thereof. The computer instructions, when executed by the processor, may cause the device to approve or deny the lab request based on the determination of whether at least one of fraud, waste, or abuse in the lab request is likely. Approving the lab request may include generating lab instructions associated with the lab request after determining whether at least one of fraud, waste, or abuse in the lab request is likely, and transmitting the lab instructions associated with the lab request to one laboratory of the plurality of medical laboratories for performance of one or more corresponding medical tests. Denying the lab request may include transmitting a lab request denial to the lab request initiator, the lab request denial indicating that the lab request needs to be revised.

In some embodiments, the pre-established data associated with the lab request may include medical history of a patient associated with the lab request, wherein the medical history of the patient includes medical tests requested by a plurality of different providers. In some embodiments, the pre-established data associated with the lab request may form a pre-established practice regarding ordering of lab requests by the plurality of medical providers. In some embodiments, the pre-established data associated with the lab request may include persistent patient data associated with the lab request.

In some embodiments, when determining whether at least one of fraud, waste, or abuse in the lab request is likely, the computer instructions, when executed by the processor, may cause the device to transmit a warning indication to a patient device associated with at least one of the plurality of patients. The warning indication may be configured to indicate that fraud, waste, abuse, or a combination thereof is suspected based on the determination of whether at least one of fraud, waste, or abuse in the lab request is likely.

In some embodiments, the computer instructions, when executed by the processor, may cause the warning indication to be transmitted prior to generating lab instructions associated with the lab request and transmitting the lab instructions associated with the lab request to one laboratory of the plurality of medical laboratories for performance of the lab instructions.

In some embodiments, when determining whether at least one of fraud, waste, or abuse in the lab request is likely, the computer instructions, when executed by the processor, may cause the device to transmit a request for additional patient data, physician data, provider data, lab data, payer data, or a combination thereof to one or more external devices operated by one or more of the plurality of medical laboratories, medical providers, lab payers, or a combination thereof.

In some embodiments, the computer instructions, when executed by the processor, may further cause the device to transmit a lab fee indication to one lab payer of the plurality of lab payers prior to generating lab instructions associated with the lab request and transmitting the lab instructions associated with the lab request to one laboratory of the plurality of medical laboratories for performance of the lab instructions.

In some embodiments, the lab request denial may include a suggested revised lab request. The suggested revised lab request may include at least one of a suggested revised medical laboratory, suggested revised medical test, or a combination thereof.

In some embodiments, the computer instructions, when executed by the processor, may further cause the device to receive a lab payment from at least one lab payer of the plurality of lab payers prior to generating lab instructions associated with the lab request.

In some embodiments, the computer instructions, when executed by the processor, may further cause the device to receive lab results from the at least one laboratory of the plurality of medical laboratories and transmit at least part of the lab payment to the at least one laboratory of the plurality of medical laboratories.

In some embodiments, the computer instructions, when executed by the processor, may further cause the device to transmit the lab results to the lab request initiator.

In another example embodiment, a method is provided for reducing fraud, waste, and abuse in the ordering and performance of medical testing across a plurality of patients, medical laboratories, medical providers, and lab payers. The method may include receiving, by a fraud, waste, and abuse circuitry, a lab request from a lab request initiator. The lab request initiator may be associated with at least one medical provider of the plurality of medical providers and the lab request may include an order for one or more medical tests to be performed. The method may also include determining, by an analytical engine, whether at least one of fraud, waste, or abuse in the lab request is likely by determining whether the lab request aligns with pre-established data associated with the lab request. The pre-established data associated with the lab request may include patient data, physician data, provider data, lab data, payer data, or a combination thereof. The method may also include approving or denying the lab request based on the determination of whether at least one of fraud, waste, or abuse in the lab request is likely. Approving the lab request may include generating, by the analytical engine, lab instructions associated with the lab request after determining whether at least one of fraud, waste, or abuse in the lab request is likely, and transmitting, by a communications interface, the lab instructions associated with the lab request to one laboratory of the plurality of medical laboratories for performance of one or more corresponding medical tests. Denying the lab request may include transmitting, by the communications interface, a lab request denial to the lab request initiator, the lab request denial indicating that the lab request needs to be revised.

In some embodiments, the pre-established data associated with the lab request may include medical history of a patient associated with the lab request, wherein the medical history of the patient includes medical tests requested by a plurality of different providers.

In some embodiments, the pre-established data associated with the lab request may form a pre-established practice regarding ordering of lab requests by the plurality of medical providers.

In some embodiments, when determining whether fraud, waste, or abuse are likely may include generating, by the analytical engine, and transmitting, by the communications interface, a warning indication to a patient device associated with at least one of the plurality of patients. The warning indication may be configured to indicate that fraud, waste, abuse, or a combination thereof is suspected.

In some embodiments, generating and transmitting the warning indication may occur prior to generating lab instructions associated with the lab request and transmitting the lab instructions associated with the lab request to one laboratory of the plurality of medical laboratories for performance of the lab instructions.

In some embodiments, the lab request denial may include a suggested revised lab request. The suggested revised lab request may include at least one of a suggested revised medical laboratory, suggested revised medical test, or a combination thereof.

In some embodiments, determining whether fraud, waste, or abuse are likely may include transmitting, by the communications interface, a request for additional patient data, physician data, provider data, lab data, payer data, or a combination thereof to one or more external devices operated by one or more of the plurality of medical laboratories, medical providers, lab payers, or a combination thereof.

In another example embodiment, a computer program product is provided including a non-transitory computer readable medium having computer program instructions stored therein, said computer program instructions, when executed by a processor, reduce fraud, waste, and abuse in the ordering and performance of medical testing across a plurality of patients, medical laboratories, medical providers, and lab payers, by causing the computer program product to receive a lab request from a lab request initiator, the lab request initiator being associated with at least one medical provider of the plurality of medical providers. The lab request may include an order for one or more medical tests to be performed. The computer program instructions, when executed by the processor, cause the computer to determine whether fraud, waste, or abuse are likely by determining whether the lab request aligns with pre-established data associated with the lab request. The pre-established data associated with the lab request may include patient data, physician data, provider data, lab data, payer data, or a combination thereof. The computer program instructions, when executed by the processor, also cause the computer to approve or deny the lab request based on the determination of whether fraud, waste, or abuse are likely. Approving the lab request may include generating lab instructions associated with the lab request after determining whether at least one of fraud, waste, or abuse in the lab request is likely, and transmitting the lab instructions associated with the lab request to one laboratory of the plurality of medical laboratories for performance of the lab instructions. Denying the lab request may include transmitting a lab request denial to the lab request initiator to revise the lab request, the lab request denial indicating that the lab request needs to be revised.

The foregoing brief summary is provided merely for purposes of summarizing some example embodiments illustrating some aspects of the present disclosure. Accordingly, it will be appreciated that the above-described embodiments are merely examples and should not be construed to narrow the scope of the present disclosure in any way. It will be appreciated that the scope of the present disclosure encompasses many potential embodiments in addition to those summarized herein, some of which will be described in further detail below.

BRIEF DESCRIPTION OF THE FIGURES

Reference will now be made to the accompanying drawings, which are not necessarily drawn to scale, and wherein.

DETAILED DESCRIPTION

Figure 1:
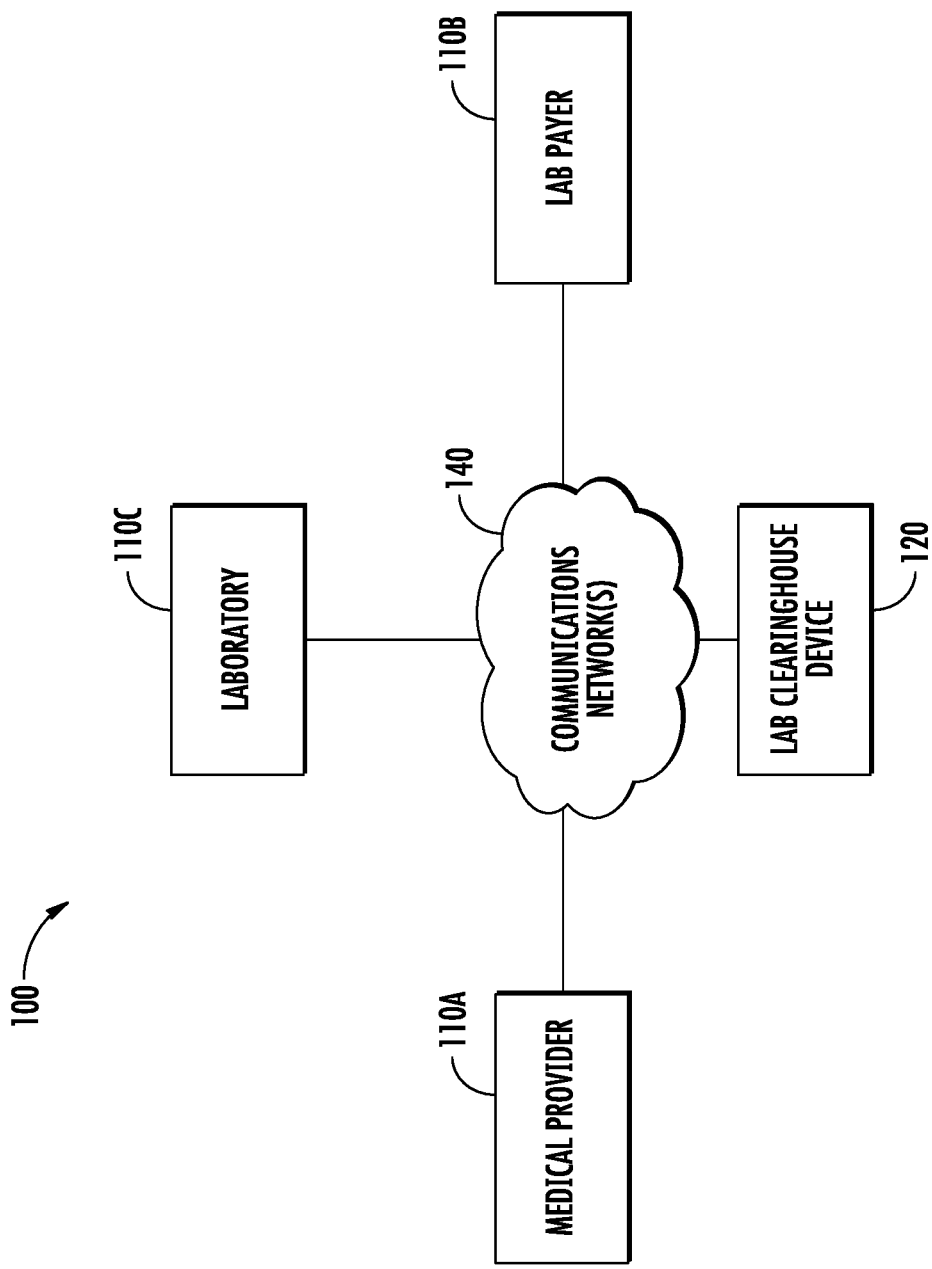
FIG. 1 illustrates an example system in accordance with some embodiments discussed herein.

Some embodiments of the present invention will now be described more fully hereinafter with reference to the accompanying drawings, in which some, but not all embodiments of the inventions are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Terms

As used herein, the terms "data," "content," "digital content," "digital content object," "information," and similar terms may be used interchangeably to refer to data capable of being transmitted, received, and/or stored in accordance with embodiments of the present invention. Thus, use of any such terms should not be taken to limit the spirit and scope of embodiments of the present invention. Further, where a computing device is described herein to receive data from another computing device, it will be appreciated that the data may be received directly from the another computing device or may be received indirectly via one or more intermediary computing devices, such as, for example, one or more servers, relays, routers, network access points, base stations, hosts, and/or the like, sometimes referred to herein as a "network." Similarly, where a computing device is described herein to send data to another computing device, it will be appreciated that the data may be sent directly to the another computing device or may be sent indirectly via one or more intermediary computing devices, such as, for example, one or more servers, relays, routers, network access points, base stations, hosts, and/or the like.

The term "client device" refers to computer hardware and/or software that is configured to access a service made available by a server. The server is often (but not always) on another computer system, in which case the client device accesses the service by way of a network. Client devices may include, without limitation, smart phones, tablet computers, laptop computers, wearables, personal computers, enterprise computers, and the like.

The term "user" should be understood to refer to an individual, group of individuals, business, organization, and the like; the users referred to herein are accessing a group-based communication or messaging system using client devices.

The terms "profile," "account," and "account details" refer to information associated with a user (e.g., patient, provider, laboratory, lab payer, etc.), including, for example, a user identifier, an email address, a real name (e.g., John Doe), a username (e.g., j doe), a password, a time zone, a status, and the like. The account details can include a subset designation of user credentials, such as, for example, login information for the user including the user's username and password.

As used herein, the term "profile identifier" refers to any data that identifies a user. For example, and without limitation, a profile identifier may include a unique identifier, an IP address, a MAC address, ASCII text, a pointer, a memory address and the like.

As used herein, the term "profile data" refers to any data associated with a profile identifier, such as, but not limited to, biographical data or any other data that may serve to characterize or describe the associated user.

As used herein, the term "biographical data" refers to information associated with a person(s) identified in a profile, such as, for example, birth dates, allergies, socio-economic data, place of residence, login credential information, and/or any other identifying information about a profile.

As used herein, the term "lab request" refers to any electronically generated digital content that is an instruction or direction, generally initiated by a user, for a medical test to be performed. For instance, the lab request can include an order for a medical test to be performed by a laboratory (e.g., a research or clinical laboratory). The lab request may order a specific medical test or a series of medical tests. The lab request may include an identification of a specific laboratory that is requested to perform the medical test or may not specify the laboratory to perform the medical test. The lab request may include a variety of information such as identifying information regarding the patient, member, and/or provider initiating the lab request, and identifying information regarding the medical test requested.

"Lab fee indication" refers to any electronically generated digital content that is an indication indicating a monetary amount identified for performance of one or more medical tests ("lab fee") ordered in a lab request.

"Lab request initiator" refers to the entity ordering some or all of the one or more medical tests listed in a lab request. The lab request initiator may be a client device operated by a physician, hospital, clinic, research facility, etc. One or more lab request initiators may be associated with a lab request. That is, a lab request may include requests for medical tests initiated by more than one lab request initiator.

The term "lab results" refers to any electronically generated digital content that represent medical test results obtained from performance of one or more corresponding medical tests. A "lab results indication" refers to any electronically generated digital content that is an indication indicating that lab results have been obtained. The lab results indication may in some embodiments include the corresponding lab results.

"Lab instructions" refers to any electronically generated digital content that is an indication typically provided to a laboratory (e.g., clinical/medical laboratory or research laboratory) that sets forth one or more medical tests to be performed. The lab instructions may include a variety of information such as requested date of completion, patient data, provider data, payer data, etc. as discussed herein. In particular, the lab instructions may include any information that may help enable the receiving laboratory to perform one or more of the medical tests indicated in the lab instructions.

"Lab payment" refers to a monetary disbursement intended to compensate for performance of one or more medical tests. A "lab payment indication" refers to any electronically generated digital content indicating that a lab payment has been provided, will be provided, or is being provided. That is, the lab payment indication may include payment details relating to a past, concurrent, or planned future payment for the one or more medical tests.

A "lab request denial" is associated with a lab request and refers to any electronically generated digital content that is an indication that one or more medical tests ordered in the associated lab request should not be ordered. For instance, in some embodiments, a lab request denial may be generated in response to the determination that the associated patient's insurance policy may not or will not cover one or more medical tests ordered in the associated lab request. The lab request denial may explain why a lab request was denied. In some embodiments, the lab request denial may not explain why a lab request was denied. The lab clearinghouse device may provide the lab request denial in real-time to the lab request initiator (e.g., the ordering physician). That is, prior to execution or performance of the medical tests requested in the lab request (and prior to generation and transmission of lab instructions), the lab request may be analyzed and a lab request denial may be generated and transmitted to the lab request initiator.

The phrase "suggested revised lab request" refers to any electronically generated digital content that is an instruction or direction, generally initiated by a user, for a medical test to be performed. The suggested revised lab request may include suggested revised medical laboratories, suggested revised medical tests, or combinations thereof that are suggested to replace or supplement the original medical laboratories or medical tests listed in a prior lab request.

A "revised lab request" refers to any modified electronically generated digital content that is an instruction or direction, generally initiated by a user, for a medical test to be performed, and which is generally generated in response to a lab request denial of a prior lab request. For instance, the revised lab request can include an order for one or more medical tests to be performed by a laboratory (e.g., a research or clinical laboratory). The revised lab request may order a specific medical test, one or more medical tests, a series of medical tests, or combinations thereof. The revised lab request may include an order for a specific laboratory to perform the medical test or may not be specific to the laboratory for performing the medical test. The revised lab request may include a variety of information such as identifying information regarding the patient, member, and/or provider associated with the lab request and identifying information regarding the medical test requested.

Communications such as lab requests, warning indications, lab fee indications, lab results, lab results indications, lab instructions, lab payments, lab request denials, revised lab requests, etc. may include any text, image, video, audio, or combination thereof provided by a user (using a client device) or by a device (such as a lab clearinghouse device). For instance, the user or device may provide a communication that includes text as well as an image and a video within the communication as communication contents. In such a case, the text, image, and video would comprise the communication or digital content object. Each communication sent in the lab clearinghouse system may include metadata comprising the following: a sending user identifier and communication contents. The sending user identifier and the communication contents may be represented by ASCII text, a pointer to a memory address, a hyperlink, or the like.

Among the specifics listed above with regard to each type of communication (e.g., lab request, warning indication, lab fee indications, lab results, lab results indication, lab instructions, lab payment, lab request denial, revised lab request, etc.), the communications may also include data such as information related to the user who created the communication, the client device on which the communication was first provided or is associated with, the time and date that the communication was first provided, additional communications stemming from the communication, and any other identifying information related to the communication.

A "sending user identifier" is associated with a communication that is sent by a particular user (i.e., a client device associated with the particular user). The sending user identifier may be analyzed to determine context regarding the user (e.g., patterns associated with the user).

The term "pre-established data" includes data associated with patients, laboratories, medical providers (e.g., physicians), lab payers, and combinations thereof that has been collected outside of the lab request. The pre-established data is data obtained prior to receipt of the lab request or after receipt of the lab request. Pre-established data may include historical data concerning one or more patients, laboratories, medical providers, and lab payers. Pre-established data may include data across one or more patients, laboratories, medical providers, and lab payers. Pre-established data may include historical data, genomic data, persistent data, profile data, location data, pricing data, or combinations thereof associated with a single patient, laboratory, medical provider, or lab payer, or across multiple patients, laboratories, medical providers, lab payers, or combinations thereof. Pre-established data may form a pre-established practice which refers to a series of one or more medical tests, lab requests, etc. that share common considerations (e.g., diagnoses) and share a common result (e.g., ordered medical tests).

A "warning indication" refers to any electronically generated digital content that indicates that fraud, waste, abuse, or combinations thereof may be associated with the associated lab request. The lab clearinghouse device may determine that one or more of fraud, waste, or abuse may be likely for one or more medical tests ordered in the lab request. A warning indication may then be generated and transmitted in response to the appropriate entity, for example, the patient (via a client device), laboratory 110C, lab payer 110B, medical provider 110A, etc.

A "request for additional data" which may be specific to the type of data requested (e.g., a "request for additional patient data", a "request for additional physician data", etc.) refers to any electronically generated digital content that requests additional information regarding a lab request (e.g., additional information regarding the implicated patient, laboratory, medical provider, lab payer, etc.). The additional information may be used in determining whether fraud, waste, or abuse are likely with regards to one or more medical tests ordered in the lab request.

Overview

Various embodiments of the invention are directed to systems, methods, devices, and computer program products that are configured to reduce fraud, waste, and abuse in laboratory orders, results, and payments within a defined system across laboratories (e.g., medical/clinical or research laboratories), lab payers, and medical providers.

Provided herein are systems, methods, devices, and computer program products to reduce fraud, waste, and abuse. To facilitate this process, a lab clearinghouse device is designed to be the intermediary in transmissions between patients, providers (e.g., physicians, hospitals, etc.), lab payers, and laboratories, and as a result, the lab clearinghouse device has access to information, e.g., electronic medical records, from each of these entities. The lab clearinghouse device may provide real-time decision support integrations with the ordering provider (e.g., individual physician, physician group, hospital, clinic, etc.) workflow, may provide real-time analysis of a lab request based on information received from the provider, member (e.g., patient), lab payer, and laboratory, and may contract with the laboratory to perform the medical tests ordered in the lab request.

The lab clearinghouse system may include a lab clearinghouse device. The lab clearinghouse device may include a lab results feedback loop that may collect genomic information as well as other persistent and historical data. The lab clearinghouse device can be used for learning and predictive analytics (e.g., prevalence of diseases based on specific genome markers). De-identified data can be sold to life sciences organizations. In an embodiment, the lab clearinghouse device can be used to trim the volume of future lab work, thus increasing the efficiency and effectiveness of the lab clearinghouse system compared to current practices. For instance, using the historical data, redundant or unnecessary labs can be avoided (e.g., by offering the results of a prior medical test instead of ordering a new medical test, warning the lab request initiator that the medical test was previously performed, or enabling the physician to see previously ordered medical tests for a specific patient). The lab clearinghouse system can thereby avoid waste, reducing costs for patients, providers, laboratories, and lab payers. Denial of payment by insurance companies due to redundant or duplicate tests can be avoided on the front end with the use of the lab clearinghouse device.

Using the lab clearinghouse device, the frequency of a medical test ordered by one physician for a certain population can be compared to other ordering physicians to identify—and thus avoid—abuse. The lab clearinghouse device can also avoid fraud (e.g., by matching the ordering physician or patient against a death file).

In some embodiments, lab results may be provided to lab payers as well as medical providers. The lab clearinghouse device may help reduce the effort associated with capturing supplemental data required for HEDIS and STARS.

Once a lab request is approved, the lab clearinghouse device may generate a lab fee indication indicating that payment for one or more medical tests is needed. Payment for the medical tests may be made, and in some embodiments, such payment may be required prior to the lab clearinghouse device initiating lab instructions associated with the underlying lab request for performance of the medical tests.

The lab clearinghouse device may be able to communicate electronic medical information (e.g., via HL7 ORU (results) and REST API) with billing systems (e.g., payments (EFT/checks)) for on-premises laboratories, payers (e.g., invoices and encounters, pre-authorization EDI 278), and laboratories (e.g., via HL7 OBM (order) and HL7 ORU (results) messages, and various payment mechanisms (EFT/checks)).

The lab clearinghouse device may allow for more accurate lab ordering, thereby reducing costs to patients, laboratories (e.g., laboratories are more likely to be reimbursed for performance of the medical tests), lab payers, and medical providers. The lab clearinghouse device may have access to a variety of information concerning patients, laboratories, lab payers, and medical providers and is thereby able to more accurately evaluate and determine whether fraud, waste, and/or abuse are likely with regards to the medical tests requested in lab requests. For instance, the lab clearinghouse device may have access to both a lab request, specifying one or more medical tests to be performed, lab instructions, and lab results. The lab clearinghouse device can evaluate whether fraud, waste, and/or abuse are likely with regards to the medical tests, and then, after communicating with the lab request initiator in some embodiments, generate and transmit lab instructions tailored to the lab request and associated data. The lab clearinghouse device may edit the lab request (e.g., through a lab request denial that provides a suggested revised lab request or through a request for additional data). The lab clearinghouse device may receive lab results thereby allowing the lab clearinghouse device to evaluate—after the fact—whether fraud, waste, and/or abuse are likely with regards to the medical tests, which can be used in determining whether fraud, waste, and/or abuse are likely with regards to future medical tests and to further tailor the lab requests and lab instructions. The lab clearinghouse device may thereby reduce fraud, waste, and abuse.

In prior systems, a lab payer may not fully understand the medical tests performed by a laboratory and typically will not have access to the provider's original order, which may lead to the lab payer inaccurately deciding to pay or not pay for a medical test or paying for more or less than what was originally requested. Similarly, in prior systems, a laboratory may not fully understand the medical tests requested by a provider which may lead to the laboratory performing more medical tests, fewer medical tests, or inappropriate medical tests. As the lab clearinghouse device analyzes the lab requests; can communicate with the lab request initiator; has access to data concerning patients, laboratories, lab payers, and medical providers and can communicate with each of these parties (via a client device); and generates and transmits the lab instructions, the lab clearinghouse device may reduce issues associated with lab payers and laboratories not fully understanding the medical tests requested. For instance, the lab clearinghouse device may be able to identify when lab instructions were not followed or when lab payments were inaccurately withheld or made.

The lab clearinghouse device may have access to information specifically concerning patients across a variety of laboratories, providers, and lab payers. The lab clearinghouse device may thereby be able to identify inappropriate or redundant medical tests requested for the patient.

The lab clearinghouse device may be configured to determine whether fraud, waste, and/or abuse are likely with regards to the medical tests prior to execution of the medical tests requested in the lab request or performance of the medical tests requested in the lab request. This proactive system may reduce fraud, waste, and abuse, thereby reducing costs and increasing efficiency. The lab clearinghouse device is rooted in computer technology in order to overcome a problem specifically arising in the realm of computer networks (e.g., lack of communication or miscommunication and mishandling of medical tests across multiple client devices and servers). Specifically, current systems for reducing fraud, waste, and abuse operate in a disjointed fashion in which various component nodes within an interconnected system (i.e., medical providers, laboratories, and payers such as insurance companies) have access to different subsets of information. To reduce fraud, waste, and abuse, these entities have to employ sophisticated software and computer tools to account for the information not known to them a priori. For instance, a medical provider is able to determine what medical tests may be required to provide appropriate care to a given patient, but is often unable to determine whether that medical test or a medical test providing comparable results has been performed on the patient in the past regardless of where the medical test was performed. Similarly, a laboratory may be unable to determine whether the requested medical tests is redundant or excessive, and may thus be forced to employ sophisticated software tools to evaluate whether the medical test will likely be deemed redundant or excessive and not paid for by the lab payer. Finally, insurance companies may not have access to the requested medical tests and rather, simply see the resulting claims from the laboratories, and may thus be forced to employ sophisticated software tools to evaluate whether the correct medical tests were performed and reported. Through the use of a lab clearinghouse system employing the lab clearinghouse device, all of this technical complexity can be avoided by the lab clearinghouse device collecting and analyzing information from these various entities in the system.

The lab clearinghouse device may in many embodiments also reduce the strain on the systems of the medical providers, laboratories, and lab payers (e.g., due to more appropriate medical testing), leading to increased adjudicatory speed and efficiency. The lab clearinghouse device may also reduce network traffic and data processing requirements by centralizing data analysis and shifting the evaluation of the lab request to the front end prior to execution or performance of the medical tests. The lab instructions may be more accurately tailored to the needs of the patient and provider, thereby reducing costs for the lab payer and the patient (e.g., by reducing denials) and for the laboratories (e.g., by avoiding redundant or excessive testing or non-reimbursable testing). For instance, with the evaluation of whether fraud, waste, and/or abuse are likely with regards to the medical tests, reimbursement by the lab payer of those tests that are performed after such an evaluation is more likely, thus leading to significant savings for the patient and laboratories (e.g., an increase in reimbursements to the laboratories of about 30% or more). The lab clearinghouse device may also increase provider engagement as the provider communicates with the lab clearinghouse device to determine the lab request (e.g., through suggested revised lab requests and revised lab requests).

Previously, patients may have had difficulty accessing lab results. However, through the use of a lab clearinghouse system predicated on a lab clearinghouse device, patients may receive lab results via the lab clearinghouse device, directly or indirectly, and may no longer need to track down lab results directly from corresponding providers or laboratories (with whom the patient may never have previously interacted).

The lab clearinghouse device may be used as part of a standalone service, application, or device or it may be applied as a layer atop an existing service application or device.

Example System Architecture

Methods, devices, and computer program products of the present invention may be embodied by any of a variety of devices. For example, the method, device, and computer program product of an example embodiment may be embodied by a networked device (e.g., an enterprise platform), such as a server or other network entity, configured to communicate with one or more devices, such as one or more client devices. Additionally or alternatively, the computing device may include fixed computing devices, such as a personal computer or a computer workstation. Still further, example embodiments may be embodied by any of a variety of mobile devices, such as a portable digital assistant (PDA), mobile telephone, smartphone, laptop computer, tablet computer, wearable, or any combination of the aforementioned devices.

FIG. 1 shows lab clearinghouse system 100 including an example network architecture for a system, which may include one or more devices and sub-systems that are configured to implement some embodiments discussed herein. For example, lab clearinghouse system 100 may include lab clearinghouse device 120, which can include, for example, the circuitry disclosed in FIGS. 2-4, one or more client devices, one or more servers, or database, among other things (not shown). The lab clearinghouse device 120 may include any suitable network server and/or other type of processing device. In some embodiments, the lab clearinghouse device 120 may receive lab requests, revised lab requests, lab payments, etc. and generate and transmit warning indications, lab instructions, lab fee indications, suggested revised lab requests, requests for additional data, etc. to external devices such as one or more medical providers 110A, laboratories 110C, and lab payers 110B using data from the lab clearinghouse data store 300 (see e.g., FIG. 2). The lab clearinghouse data store 300 may be embodied as a data storage device such as a Network Attached Storage (NAS) device or devices, as a separate database server or servers (e.g., cloud computing), or distributed across multiple devices in a network (e.g., blockchain). The lab clearinghouse data store 300 stores information for the lab clearinghouse device 120 to facilitate the operations of the lab clearinghouse system 100. For example, the lab clearinghouse data store 300 may include, without limitation, a plurality of data regarding patients, medical tests, laboratories, medical providers, lab payers, etc., organized within the lab clearinghouse data store 300.

Lab clearinghouse device 120 can communicate with one or more medical providers 110A, laboratories 110C, and lab payers 110B, each of which may include one or more client devices and/or servers, via network 140. In this regard, network 140 may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, network 140 may include a cellular telephone, an 802.11, 802.16, 802.20, and/or WiMax network. Further, the network 140 may include a public network, such as the Internet, a private network, such as an intranet, or combinations thereof, and may utilize a variety of networking protocols now available or later developed including, but not limited to TCP/IP based networking protocols. For instance, the networking protocol may be customized to suit the needs of the lab clearinghouse device 120 and/or lab clearinghouse system 100.

The lab clearinghouse device 120 may provide for receiving of electronic data from various sources, including but not necessarily limited to one or more medical providers 110A, laboratories 110C, and lab payers 110B, via for instance client devices or servers within the one or more medical providers 110A, laboratories 110C, and lab payers 110B. For example, the lab clearinghouse device 120 may be operable to receive and post or transmit communications provided by the one or more medical providers 110A, laboratories 110C, and lab payers 110B.

Lab clearinghouse device 120, medical providers 110A, laboratories 110C, and lab payers 110B may each be implemented as a personal computer and/or other networked device, such as a cellular phone, tablet computer, mobile device, desktop computer, laptop computer, smartphone, netbook, wearable, and the like, that may be used for any suitable purpose in addition to processing lab requests, lab results, and lab payments, etc. The depiction in FIG. 1 of one medical provider 110A, one lab payer 110B, and one laboratory 110C is merely for illustration purposes. Any number of medical providers 110A, lab payers 110B, and laboratories 110C may be included in the lab clearinghouse system 100. In one embodiment, the medical providers 110A, lab payers 110B, and laboratories 110C may be configured to display an interface on a display of the respective device for viewing, creating, editing, and/or otherwise interacting with the lab clearinghouse device 120. According to some embodiments, the lab clearinghouse device 120 may be configured to display an interface on a display of the lab clearinghouse device 120 for viewing, creating, editing, and/or otherwise interacting with the medical providers 110A, lab payers 110B, and laboratories 110C. In some embodiments, an interface of a medical provider 110A, lab payer 110B, and laboratory 110C may be the same or different from an interface of a lab clearinghouse device 120. Lab clearinghouse system 100 may also include additional client devices and/or servers, among other things. Additionally or alternatively, the lab clearinghouse device 120, medical providers 110A, lab payers 110B, and laboratories 110C may interact within the lab clearinghouse system 100 via a web browser. As yet another example, the lab clearinghouse device 120, medical providers 110A, lab payers 110B, and laboratories 110C may include various hardware or firmware designed to interface with the various other devices within the lab clearinghouse system 100.

The lab clearinghouse device 120, medical providers 110A, lab payers 110B, and laboratories 110C may be any computing device as defined above. Electronic data received by the lab clearinghouse device 120 from the medical providers 110A, lab payers 110B, and laboratories 110C may be provided in various forms and via various methods. Electronic data received by the medical providers 110A, lab payers 110B, and laboratories 110C from the lab clearinghouse device 120 may be provided in various forms and via various methods. For example, the lab clearinghouse device 120 may be able to communicate with electronic medical records (e.g., HL7 ORU (results) and REST API), with billing systems (e.g., payments (EFT/checks)) for on-premise laboratories, payers (e.g., invoices and encounters, pre-authorization EDI 278), and laboratories (e.g., HL7 OBM (order) and HL7 ORU (results), and payments (EFT/checks)).

In embodiments where any of the lab clearinghouse device 120, medical provider 110A, lab payer 110B, and laboratory 110C is a mobile device, such as a smart phone or tablet, the respective client device may execute an "app" to operate within the lab clearinghouse system 100. Such apps are typically designed to execute on mobile devices, such as tablets or smartphones. For example, an app may be provided that executes on mobile device operating systems such as iOS®, Android®, or Windows®. These platforms typically provide frameworks that allow apps to communicate with one another and with particular hardware and software components of mobile devices. For example, the mobile operating systems named above each provide frameworks for interacting with location services circuitry, wired and wireless network interfaces, user contacts, and other applications. Communication with hardware and software circuitries executing outside of the app is typically provided via application programming interfaces (APIs) provided by the mobile device operating system.

Additionally or alternatively, the lab clearinghouse device 120, medical provider 110A, lab payer 110B, and laboratory 110C may interact with other devices within the lab clearinghouse system 100 via a web browser.

In some embodiments of an exemplary system, a communication (e.g., a lab request, lab instructions, lab fee indication, lab payment indication, lab request denial, warning indication, request for additional data, patient data, provider data, physician data, payer data, etc.) may be sent from a medical provider 110A, lab payer 110B, and/or laboratory 110C to a lab clearinghouse device 120. In various implementations, the communication may be sent directly to the lab clearinghouse device 120 (e.g., via a peer-to-peer connection) or over a network 140, in which case the communication may in some embodiments be transmitted via an intermediary such as a message server, and/or the like. In one implementation, the communication may include data such as a sending user identifier, communication contents (e.g., text, emojis, images, links), attachments (e.g., files), communication hierarchy data (e.g., whether the communication is a reply to another communication), metadata, and/or the like.

The lab clearinghouse system 100 may include a server (e.g., as part of the lab clearinghouse device 120) that may store communications, which may be indexed, in a lab clearinghouse data store 300. In some embodiments, a storage communication may be generated and stored in remote storage (e.g., cloud storage). In one implementation, the storage communication may include data such as a sending user identifier, communication contents, attachments, message hierarchy data, metadata, and/or the like.

In one implementation, the communication may be parsed by the lab clearinghouse device 120 to identify various components included therein. Parsing of the communication may facilitate determination by the lab clearinghouse device 120 of a sending user identifier of the user who sent the message and/or to the contents of the communication and to what or whom the communication relates.

Similarly, parsing of the communication enables the lab clearinghouse device 120 to determine topics discussed in the message (e.g., medical tests, lab results, lab payments, lab fees, etc.). In another example, the communication may be analyzed (e.g., by itself, or with other communications) or parsed using a machine learning technique, such as topic modeling, to determine topics associated with the message. The topics may help provide context for the communication such that the lab clearinghouse device 120 and other components of the lab clearinghouse system 100 may generate an appropriate response.

In some embodiments, attachments may be included with the communication. If there are attachments, files may be associated with the communication. In one implementation, the communication may be parsed to determine information regarding the attachments, such as file names and contents, which may in turn be analyzed to determine the context of the communication (e.g., to determine whether the communication relates to a lab fee, lab payment, lab results, etc.).

In embodiments, metadata may be associated with the communication. For example, metadata may provide additional context regarding the communication or the user that is specific to a company, organization, and/or the like. In one implementation, the communication may be parsed to determine metadata. For example, metadata may provide data regarding the user who sent the communication.

In embodiments, various metadata, determined as described above, and/or the contents of the communication may be used to index the communication to facilitate various facets of searching (i.e., search queries that return results from lab clearinghouse data store 300). In one implementation, a communication may be sent from lab clearinghouse device 120 to facilitate indexing in the lab clearinghouse data store 300. In another implementation, metadata associated with the communication may be determined and the communication may be indexed in the lab clearinghouse data store 300. In one embodiment, the communication may be indexed such that an entity's communications are indexed separately (e.g., in a separate index associated with the patient, medical provider, laboratory, lab payer, etc. that is not shared with other patients, medical providers, laboratories, lab payers, etc.). In one implementation, communications may be indexed at a separate distributed database (e.g., to facilitate data isolation for security purposes).

If there are attachments associated with the communication, file contents of the associated files may be used to index such files in the lab clearinghouse data store 300 to facilitate searching. In one embodiment, the files may be indexed such that files for a patient, medical provider, laboratory, lab payer, etc. are indexed at a separate distributed database.

Figure 2:
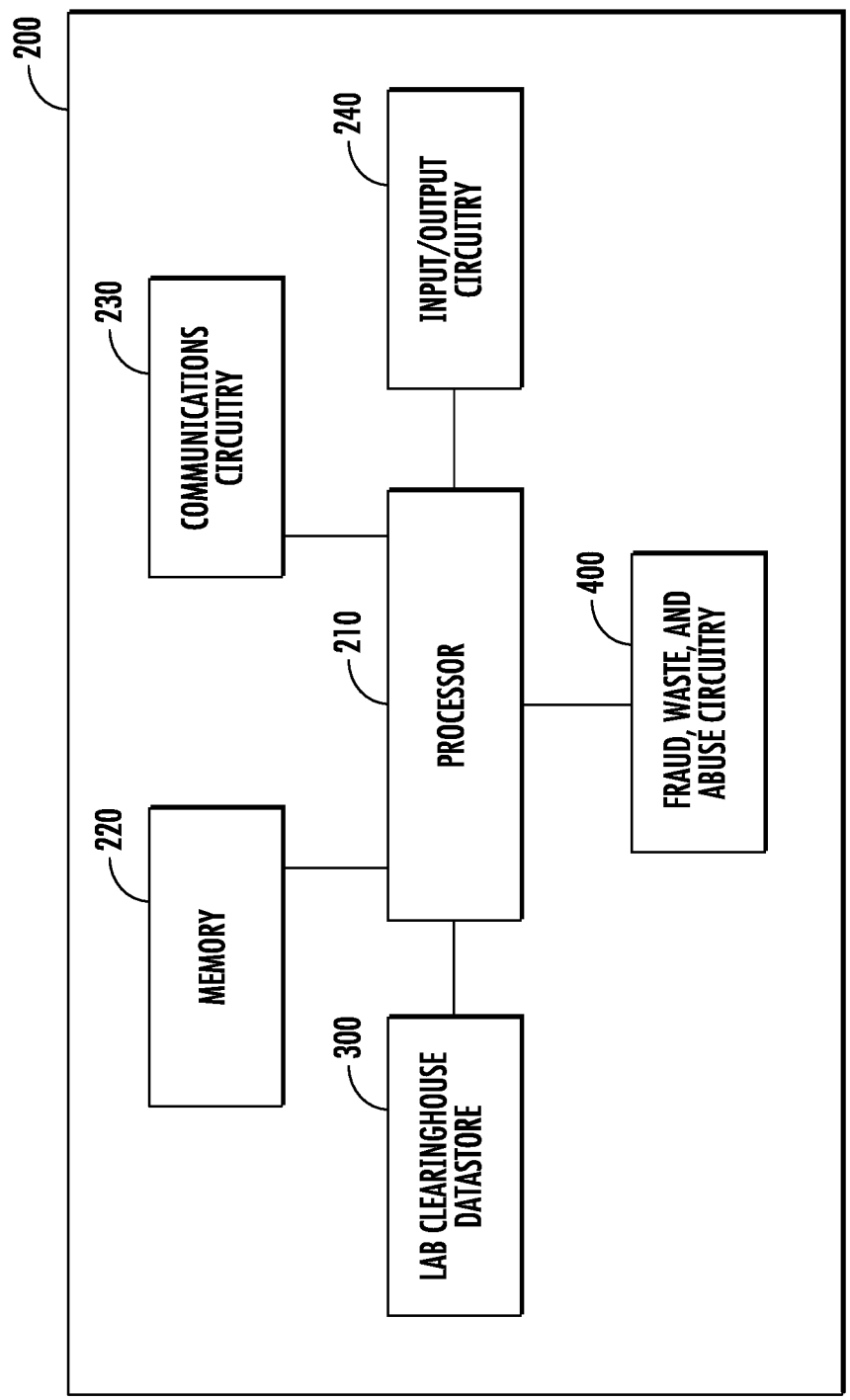
FIG. 2 illustrates a schematic block diagram of circuitry that can be included in a computing device in accordance with some embodiments discussed herein.
Figure 3:
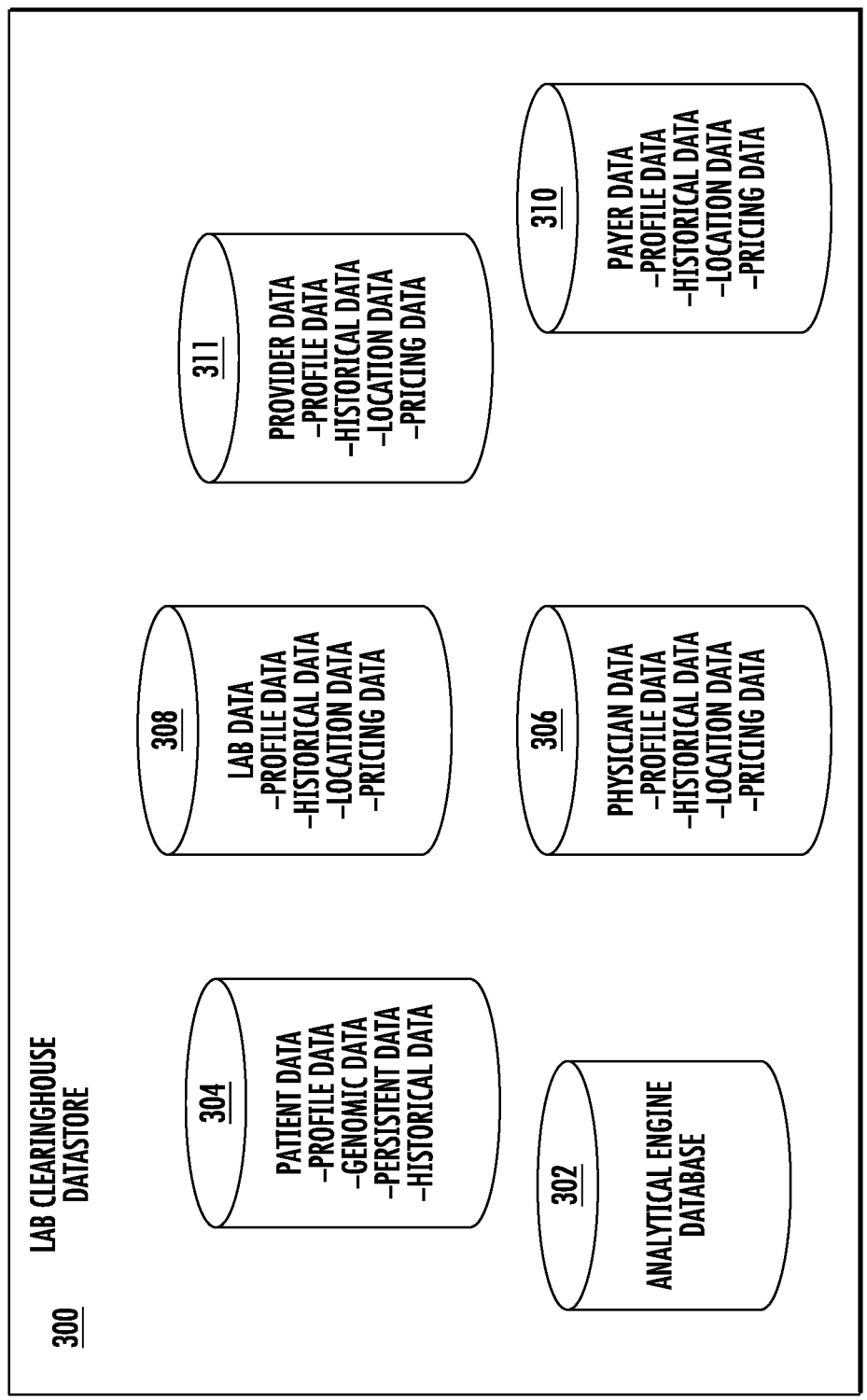
FIG. 3 illustrates an example lab clearinghouse data store in accordance with some embodiments discussed herein.

FIG. 2 shows a schematic block diagram of an apparatus 200, some or all of the components of which may be included, in various embodiments, in lab clearinghouse device 120 and/or medical provider 110A, lab payer 110B, and laboratory 110C. Any of the aforementioned systems or devices may include the components of apparatus 200 and may be configured to, either independently or jointly with other devices in a lab clearinghouse system 100, to perform the functions of the apparatus 200 described herein. As illustrated in FIG. 2, in accordance with some example embodiments, apparatus 200 can includes various means, such as processor 210, memory 220, communications circuitry 230, and/or input/output circuitry 240. In some embodiments, lab clearinghouse data store 300 and/or fraud, waste, and abuse circuitry 400 may also or instead be included. As referred to herein, "circuitry" includes hardware, or a combination of hardware with software configured to perform one or more particular functions. In this regard, the various components of apparatus 200 described herein may be embodied as, for example, circuitry, hardware elements (e.g., a suitably programmed processor, combinational logic circuit, and/or the like), a computer program product comprising computer-readable program instructions stored on a non-transitory computer-readable medium (e.g., memory 220) that is executable by a suitably configured processing device (e.g., processor 210), or some combination thereof. In some embodiments, one or more of these circuitries may be hosted remotely (e.g., by one or more separate devices or one or more cloud servers) and thus need not reside on the data set device or user device. The functionality of one or more of these circuitries may be distributed across multiple computers across a network.

Processor 210 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an ASIC (application specific integrated circuit) or FPGA (field programmable gate array), or some combination thereof. Accordingly, although illustrated in FIG. 2 as a single processor, in some embodiments processor 210 comprises a plurality of processors. The plurality of processors may be embodied on a single computing device or may be distributed across a plurality of computing devices collectively configured to function as apparatus 200. The plurality of processors may be in operative communication with each other and may be collectively configured to perform one or more functionalities of apparatus 200 as described herein. In an example embodiment, processor 210 is configured to execute instructions stored in memory 220 or otherwise accessible to processor 210. These instructions, when executed by processor 210, may cause apparatus 200 to perform one or more of the functionalities as described herein.

Whether configured by hardware, or a combination of hardware with firmware/software methods, processor 210 may comprise an entity capable of performing operations according to embodiments of the present invention while configured accordingly. Thus, for example, when processor 210 is embodied as an ASIC, FPGA or the like, processor 210 may comprise the specifically configured hardware for conducting one or more operations described herein. Alternatively, as another example, when processor 210 is embodied as an executor of instructions, such as may be stored in memory 220, the instructions may specifically configure processor 210 to perform one or more algorithms and operations described herein, such as those discussed in connection with FIGS. 5-8.

Memory 220 may comprise, for example, volatile memory, non-volatile memory, or some combination thereof. Although illustrated in FIG. 2 as a single memory, memory 220 may comprise a plurality of memory components. The plurality of memory components may be embodied on a single computing device or distributed across a plurality of computing devices. In various embodiments, memory 220 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof. Memory 220 may be configured to store information, data (including item data and/or profile data), applications, instructions, or the like for enabling apparatus 200 to carry out various functions in accordance with example embodiments of the present invention. For example, in at least some embodiments, memory 220 is configured to buffer input data for processing by processor 210. Additionally or alternatively, in at least some embodiments, memory 220 is configured to store program instructions for execution by processor 210. Memory 220 may store information in the form of static and/or dynamic information. This stored information may be stored and/or used by apparatus 200 during the course of performing its functionalities.

Communications circuitry 230 may be embodied as any device or means embodied in circuitry, hardware, a computer program product comprising computer readable program instructions stored on a computer readable medium (e.g., memory 220) and executed by a processing device (e.g., processor 210), or a combination thereof that is configured to receive and/or transmit data from/to another device and/or network, such as, for example, a second apparatus 200 and/or the like. In some embodiments, communications circuitry 230 (like other components discussed herein) can be at least partially embodied as or otherwise controlled by processor 210. In this regard, communications circuitry 230 may be in communication with processor 210, such as via a bus. Communications circuitry 230 may include, for example, an antenna, a transmitter, a receiver, a transceiver, network interface card and/or supporting hardware and/or firmware/software for enabling communications with another computing device. Communications circuitry 230 may be configured to receive and/or transmit any data that may be stored by memory 220 using any protocol that may be used for communications between computing devices. Communications circuitry 230 may additionally or alternatively be in communication with the memory 220, input/output circuitry 240 and/or any other component of apparatus 200, such as via a bus.

Input/output circuitry 240 may be in communication with processor 210 to receive an indication of a user input and/or to provide an audible, visual, mechanical, or other output to a user (e.g., provider and/or consumer). Some example visual outputs that may be provided to a user by apparatus 200 are discussed in connection with FIGS. 1-8. As such, input/output circuitry 240 may include support, for example, for a keyboard, a mouse, a joystick, a display, a touch screen display, a microphone, a speaker, a RFID reader, barcode reader, biometric scanner, and/or other input/output mechanisms. In embodiments wherein apparatus 200 is embodied as a server or database, aspects of input/output circuitry 240 may be reduced as compared to embodiments where apparatus 200 is implemented as an end-user machine (e.g., lab payer device and/or provider device) or other type of device designed for complex user interactions. In some embodiments (like other components discussed herein), input/output circuitry 240 may even be eliminated from apparatus 200. Alternatively, such as in embodiments wherein apparatus 200 is embodied as a server or database, at least some aspects of input/output circuitry 240 may be embodied on an apparatus used by a user that is in communication with apparatus 200. Input/output circuitry 240 may be in communication with the memory 220, communications circuitry 230, and/or any other component(s), such as via a bus. One or more than one input/output circuitry and/or other component can be included in apparatus 200.

Lab clearinghouse data store 300 and fraud, waste, and abuse circuitry 400 may also or instead be included and configured to perform the functionality discussed herein related to storing, generating, and/or editing communications. In some embodiments, some or all of the functionality of these components of the apparatus 200 may be performed by processor 210, although in some embodiments, these components may include distinct hardware circuitry designed to perform their respective functions. In this regard, the example processes and algorithms discussed herein can be performed by at least one processor 210, lab clearinghouse data store 300, and/or fraud, waste, and abuse circuitry 400. For example, non-transitory computer readable media can be configured to store firmware, one or more application programs, and/or other software, which include instructions and other computer-readable program code portions that can be executed to control each processor (e.g., processor 210, lab clearinghouse data store 300, and fraud, waste, and abuse circuitry 400) of the components of apparatus 200 to implement various operations, including the examples shown above. As such, a series of computer-readable program code portions are embodied in one or more computer program goods and can be used, with a computing device, server, and/or other programmable apparatus, to produce machine-implemented processes.

In some embodiments, the lab clearinghouse data store 300 may store patient data 304, lab data 308, physician data 306, payer data 310, provider data 311, and/or analytical engine data 302. Patient data 304 may include various information, such as profile data (e.g., preference data, name, address, contact information, insurance provider, etc.), genomic data (e.g., genomic test results), persistent data (e.g., sex, birthdate, race, date of death, etc.), historical data (e.g., past disease conditions, medical tests and results, surgeries, family medical data, etc.) particular to the patient (e.g., regardless of the medical provider, laboratory, and lab payer). This data may be retrieved from any of a variety of sources, such as from any of a number of medical providers 110A, lab payers 110B, or laboratories 110C, from a patient via a separate patient terminal (not shown in FIG. 1), or from any of a number of other third party devices that may be connected to the lab clearinghouse device 120. Lab data 308 may include various information, such as profile data (e.g., preference data, name, address, contact information, etc.), historical data (e.g., prior labs performed, etc.), location data (e.g., region, state, etc.), and pricing data (e.g., current pricing structure, past pricing structure, etc.) particular to a laboratory (e.g., regardless of the medical provider, patient, and lab payer). This data may most likely be retrieved from the laboratory to which it relates, although in some embodiments this data may also be retrieved from other sources who interact with the laboratory and thus acquire information regarding the various practices of the laboratory. Provider data 311 may include various information, such as profile data (e.g., preference data, name, address, contact information, etc.), historical data (e.g., prior labs requested, etc.), location data (e.g., region, state, etc.), and pricing data (e.g., current pricing structure, past pricing structure, etc.) particular to the medical provider (e.g., regardless of the patient, laboratory, and lab payer). As with the patient data 304 and laboratory data 308, this provider data 311 may be retrieved from a wide variety of sources, such as any of the devices that may interact with the lab clearinghouse 120. Finally, through similar sources, the lab clearinghouse data store 300 may acquire and store physician data 306, which may be more specific to individual physicians (rather than a group of physicians which may be referred to as a single provider) and may include various information, such as profile data (e.g., preference data, name, address, contact information, etc.), historical data (e.g., prior labs requested, etc.), location data (e.g., region, state, etc.), and pricing data (e.g., current pricing structure, past pricing structure, etc.) particular to the physician (e.g., regardless of the medical provider (e.g., hospital or physician group), patient, laboratory, and lab payer), and payer data 310, which may include various information, such as profile data (e.g., preference data, name, address, contact information, etc.), historical data (e.g., prior payments, prior policies, etc.), location data (e.g., region, state, etc.), and pricing data (e.g., current payment policy, etc.) particular to a lab payer (e.g., regardless of the provider, patient, and laboratory). Additionally or alternatively, the lab clearinghouse data store 300 may include analytical engine data 302 which provides any additional information needed by the processor 210 in analyzing and generating communications.

Overlap among the data obtained by the lab clearinghouse data store 300 among the patient data 304, lab data 308, physician data 306, payer data 310, provider data 311, and/or analytical engine data 302 may occur and information from one or more of these databases may be retrieved from the medical provider 110A, lab payer 110B, and laboratory 110C to support the fraud, waste, and abuse circuitry 400. Additionally or alternatively, the lab clearinghouse data store 300 may include analytical engine data 302 which provides any additional information needed by the processor 210 in analyzing and generating communications. Requests for additional data may be transmitted by the lab clearinghouse device 120 to the appropriate medical provider 110A, lab payer 110B, laboratory 110C, or combinations thereof to obtain additional information needed in evaluating the lab request. The additional data may be stored in the lab clearinghouse data store 300.

Fraud, waste, and abuse circuitry 400 can be configured to analyze multiple sets of requests, indications, lab payments, lab fees, data, other communications discussed herein and combinations thereof, such as any combination of the data in the lab clearinghouse data store 300. In this way, fraud, waste, and abuse circuitry 400 may execute multiple algorithms, including those discussed below with respect to the lab clearinghouse system 100.

Figure 4:
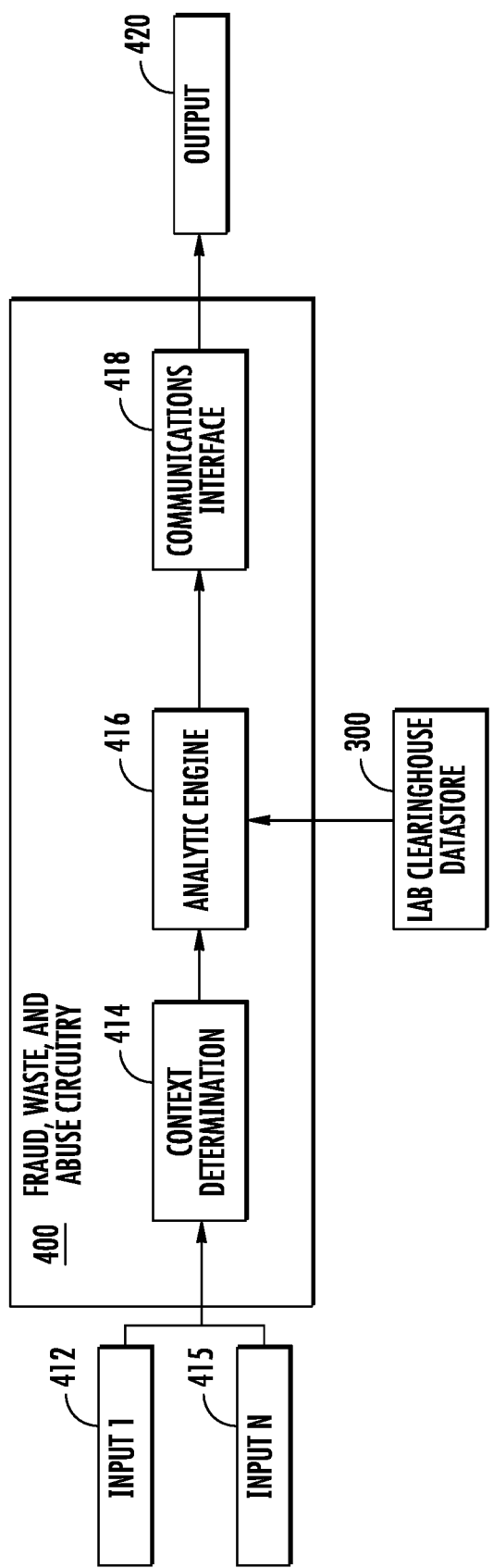
FIG. 4 illustrates example fraud, waste, and abuse circuitry in accordance with some embodiments discussed herein.

In some embodiments, with reference to FIG. 4, the fraud, waste, and abuse circuitry 400 may include a context determination circuitry 414, an analytical engine 416, and communications interface 418, all of which may be in communication with the lab clearinghouse data store 300. In some embodiments, the context determination module 414 may be implemented using one or more of the components of apparatus 200. For instance, the context determination module 414 may be implemented using one or more of the processor 210, memory 220, communications circuitry 230, and input/output circuitry 240. For instance, the context determination module 414 may be implemented using one or more of the processor 210 and memory 220. The analytical engine 416 may be implemented using one or more of the processor 210, memory 220, communications circuitry 230, and input/output circuitry 240. For instance, the analytical engine 416 may be implemented using one or more of the processor 210 and memory 220. The communications interface 418 may be implemented using one or more of the processor 210, memory 220, communications circuitry 230, and input/output circuitry 240. For instance, the communications interface 418 may be implemented using one or more of the communications circuitry 230 and input/output circuitry 240.

The fraud, waste, and abuse circuitry 400 may receive one or more communications (e.g., lab requests, lab payments, lab results indications, revised lab requests, relevant data etc.) and may generate the appropriate communications (e.g., lab fee indication, lab instructions, lab request denial, suggested revised lab request, warning indication, etc.) in response. The fraud, waste, and abuse circuitry 400 may use any of the algorithms or processes disclosed herein for receiving any of the requests, indications, payments, fees, data, etc. discussed herein and generating the appropriate communications and/or data in response. In some other embodiments, such as when the apparatus 200 is embodied in a server and/or client devices, the fraud, waste, and abuse circuitry 400 may be located in another apparatus 200 or another device, such as another server and/or client devices.

The fraud, waste, and abuse circuitry 400 can be configured to access data corresponding to multiple medical providers 110A, lab payers 110B, laboratories 110C, patients, physicians, etc., and generate one or more appropriate requests, indications, lab fees, lab payments, data, and/or other communications in response.

The system may receive a plurality of inputs 412, 415 from the apparatus 200 and process the inputs within the fraud, waste, and abuse circuitry 400 to produce an output 420, which may include appropriate requests, indications, lab fees, lab payments, data, and/or other communications in response. In some embodiments, the fraud, waste, and abuse circuitry 400 may execute context determination using the context determination circuitry 414, process the communication and/or data in an analytical engine 416, and output the results via a communications interface 418. Each of these steps may retrieve data from a variety of sources including the lab clearinghouse data store 300.

When inputs 412, 415 are received by the fraud, waste, and abuse circuitry 400, the context determination circuitry 414 may make a context determination regarding the communication. A context determination includes such information as a user preference data, when and what user initiated generation of the input (e.g., when and who selected the actuator that initiated the lab request), what type of input was provided (e.g., was a lab request initiated or a revised lab request initiated) and under what circumstances receipt of the input was initiated (e.g., patient data, provider data, etc. related to the input). This information may give context to the fraud, waste, and abuse circuitry 400 analysis for subsequent determinations. For example, the context determination circuitry 414 may inform the fraud, waste, and abuse circuitry 400 as to the communication content to output with a communication.

The fraud, waste, and abuse circuitry 400 may then compute the output using the analytical engine 416. The analytical engine 416 draws the applicable data from the lab clearinghouse data store 300 and then, based on the context determination made by the context determination circuitry 414, computes an output, which may vary based on the input. The communications interface 418 then outputs the output 420 to the apparatus 200 for display on the appropriate device. For instance, the context determination circuitry 414 may determine that a lab request was received from a medical provider 110A. Based on this information as well as the applicable data from the lab clearinghouse data store 300 (e.g., patient data, provider data, payer data, etc.), the analytical engine 416 may determine an appropriate output 420, such as whether a lab request denial should be generated and transmitted to the lab request initiator, whether a lab fee indication should be generated and transmitted to a lab payer 110B, whether lab instructions should be generated and transmitted to a laboratory 110C, whether a warning indication should be generated and transmitted to any one of the lab request initiator, medical provider 110A (if not the lab request initiator), lab payer 110B, or laboratory 110C, etc. The analytical engine 416 may also determine that certain data in the lab clearinghouse data store 300 should be updated to reflect the new information contained in the received input. Similarly, the context determination circuitry 414 may determine that a revised lab request, lab payment, lab results indication, or the like was received, and may further determine whether any additional contextual information was received, and the analytical engine 416 may determine the appropriate output based on this information as well as additional information from the lab clearinghouse data store 300, as further described herein.

As will be appreciated, any such computer program instructions and/or other type of code may be loaded onto a computer, processor or other programmable apparatus's circuitry to produce a machine, such that the computer, processor other programmable circuitry that execute the code on the machine create the means for implementing various functions, including those described herein.

It is also noted that all or some of the information presented by the example devices and systems discussed herein can be based on data that is received, generated and/or maintained by one or more components of a local or networked system and/or apparatus 200. In some embodiments, one or more external systems (such as a remote cloud computing and/or data storage system) may also be leveraged to provide at least some of the functionality discussed herein.

As described above and as will be appreciated based on this disclosure, embodiments of the present invention may be configured as methods, personal computers, servers, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Example Operations of the Lab Clearinghouse System

Figure 5:
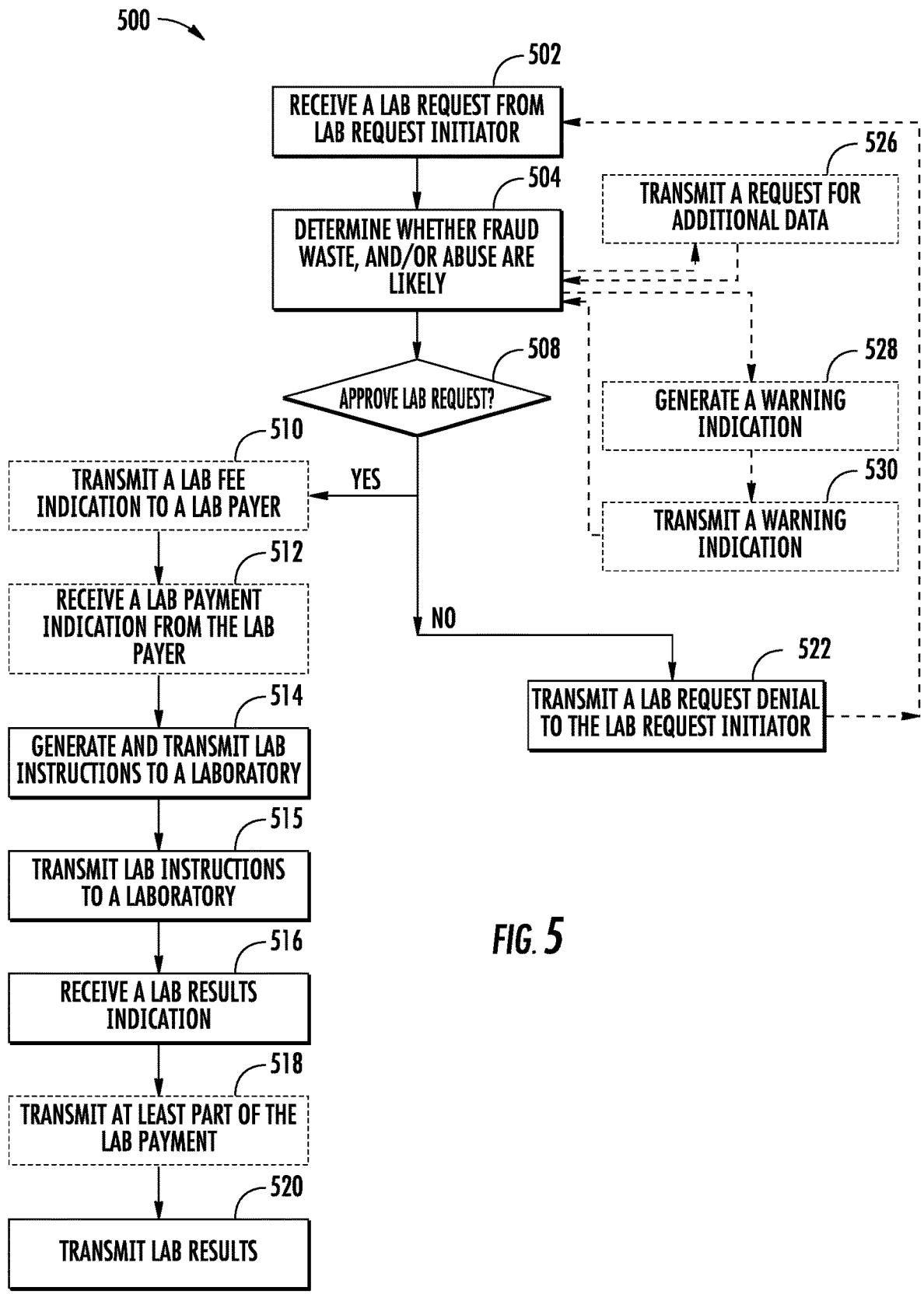
FIG. 5 illustrates a flow diagram of exemplary operations of a lab clearinghouse system in accordance with some embodiments discussed herein.

FIG. 5 illustrates a flow diagram of an example lab clearinghouse system for reducing fraud, waste, and abuse in accordance with some embodiments discussed herein.

The operations illustrated in FIG. 5 may, for example, be performed by, with the assistance of, and/or under the control of an apparatus 200, as described above. In this regard, performance of the operations may invoke one or more of processor 210; memory 220; input/output circuitry 240; communications circuitry 230; lab clearinghouse data store 300; and/or fraud, waste, and abuse circuitry 400 (e.g., context determination circuitry 414, analytical engine 416, and/or communications interface 418).

As shown in operation 502, the apparatus 200 includes means, such as processor 210, memory 220, input/output circuitry 240, communications circuitry 230, fraud, waste, and abuse circuitry 400, or the like, for receiving a lab request from a lab request initiator (502). In one such embodiment, input/output circuitry 240 may receive a lab request from a user, whereas in another such embodiment, communications circuitry 208 may receive data from another device. In some embodiments, the lab request initiator may be a medical provider and may be specific to a single physician, a group of physicians, a hospital, or other collection of medical providers with the credentials to order medical testing of a patient or patient's specimen. The lab request may request the performance of one or more medical tests and may include various information relevant to the medical tests, patient, lab request initiator, laboratory for performing the medical tests, etc.

Thereafter, as shown in operation 504, the apparatus 200 includes means, such as processor 210; memory 220; lab clearinghouse data store 300; fraud, waste, and abuse circuitry 400 (e.g., context determination circuitry 414, analytical engine 416, and/or communications interface 418); or the like, for determining whether fraud, waste, and/or abuse are likely with regards to the lab request (504).

The determination of whether fraud, waste, and/or abuse are likely with regards to the lab request may be performed in real time. That is, after receipt of the lab request, the lab clearinghouse device 120 may determine whether fraud, waste, and/or abuse are likely with regards to the lab request prior to transmitting lab instructions to a laboratory 110C for performance of the medical tests requested in the lab request. The lab clearinghouse device has access to a variety of information that may allow for determining whether fraud, waste, and/or abuse are likely with regards to the lab request prior to execution or performance of the medical tests requested in the lab request.

When determining whether fraud, waste, and/or abuse are likely with regards to the lab request, the lab clearinghouse device 120 may request additional information from various entities, such as the patient, laboratory 110C, lab payer 110B, medical provider 110A, etc. As shown in operation 526, the apparatus 200 may include means, such as processor 210; memory 220; input/output circuitry 240; communications circuitry 230; lab clearinghouse data store 300; fraud, waste, and abuse circuitry 400 (e.g., context determination circuitry 414, analytical engine 416, and/or communications interface 418); or the like, for transmitting a request for additional data (526) to any of the entities discussed herein (e.g., patient, laboratory 110C, lab payer 110B, medical provider 110A, etc.). The request for additional data may specify the information requested and such information may enable the apparatus 200 to determine whether fraud, waste, and/or abuse are likely with regards to the lab request. For instance, in some embodiments, both the lab clearinghouse device 120 and the lab payer 110B may communicate to determine whether fraud, waste, and/or abuse are likely with regards to the lab request prior to execution or performance of the medical tests requested in the lab request.

In some embodiments, the lab clearinghouse device 120 may determine whether fraud, waste, and/or abuse are likely by determining whether the lab request aligns with pre-established data associated with the lab request. For instance, in some embodiments, the lab clearinghouse device 120 may determine, based on an analysis of the lab request; the medical tests ordered in the lab request; the patient, physician, provider, lab payer, or laboratory data associated with the lab request; or combinations thereof, that the performance of the medical tests requested in the lab request may be wasteful. In some embodiments, based on this analysis, the lab clearinghouse device 120 may determine that the ordering of the medical tests requested in the lab request may be an abuse of discretion. In some embodiments, based on this analysis, the lab clearinghouse device 120 may determine that the ordering of the medical tests requested in the lab request may be fraudulent. Some example procedures by which the lab clearinghouse device 120 may make these determinations are outlined below.

The pre-established data may include patient data, physician data, provider data, lab data, payer data, or a combination thereof. The lab clearinghouse device has access to historical data in each of these categories and can use such data for learning and predictive analytics (e.g., prevalence of diseases such as based on specific genome markers) to determine whether fraud, waste, or abuse are likely or not (in which case the lab request should be modified or discarded and a warning indication may be generated and transmitted). For instance, the pre-established data may include patient data (e.g., a radius of location where the patient lives, whether the patient is male or female, the age of the patient, prior diagnosis, etc.) and may be used to evaluate whether fraud, waste, or abuse are likely. For instance, if the pre-established data indicates that the patient lives in the southeast and the lab request is from a lab request initiator located in the northwest, then a comparison of the pre-established data and the lab request would indicate that the two do not align and fraud, waste, or abuse may be likely (a warning indication may be generated and transmitted to the patient (via a client device)). Similarly, if the pre-established data indicates that the patient is a male and the lab request is for medical tests typically requested for females, then a comparison of the pre-established data and the lab request would indicate that the two do not align and fraud, waste, or abuse may be likely (a warning indication may be generated and transmitted to the patient (via a client device)). Similarly, if the pre-established data indicates that the patient is young and the lab request is for medical tests typically requested for older patients, then a comparison of the pre-established data and the lab request would indicate that the two do not align and fraud, waste, or abuse may be likely (a warning indication may be generated and transmitted to the patient (via a client device)). Similarly, if the pre-established data indicates that the patient was previously diagnosed with a certain condition and the lab request is for medical tests that would not be suitable for a patient with such condition, then a comparison of the pre-established data and the lab request would indicate that the two do not align and fraud, waste, or abuse may be likely (a warning indication may be generated and transmitted to the patient (via a client device)). Similarly, if the pre-established data indicates that certain medical tests were previously performed on the patient or patient's specimen and the lab request is for those same medical tests, then a comparison of the pre-established data and the lab request would indicate that the two do not align and fraud, waste, or abuse may be likely (a warning indication may be generated and transmitted to the patient and/or lab request initiator (via a client device)).

The pre-established data may form a pre-established practice and may be used to evaluate whether fraud, waste, or abuse are likely with regards to a lab request. The pre-established practice may be associated with a different patient, provider (e.g., physician), laboratory, lab payer, etc.

than that of the lab request being evaluated. For instance, a plurality of providers may request certain medical tests with certain patients/diagnoses. The occurrence of these requests may form a pre-established practice that can then be used to evaluate whether the present lab request aligns with the pre-established practice. If the present lab request does not include the medical tests typically ordered for similar patients/diagnoses, includes more medical tests than typically ordered, or includes more expensive medical tests than typically ordered, then fraud, waste, or abuse may be likely (a warning indication may be generated and transmitted to the patient (via a client device)).

By comparing the lab request to the pre-established data (e.g., patient data, pattern of medical tests, etc.), the lab clearinghouse device 120 may determine that fraud, waste, or abuse are likely. For instance, the patient data or pre-established practices across similar patients may indicate that the presently requested medical tests may be wasteful (e.g., redundant, would not actually provide the desired information, or would provide more information than needed), an abuse of power (e.g., clearly not needed in view of prior medical tests), or fraudulent (e.g., intentionally redundant or not needed, such as if the patient is deceased, lives in another part of the country, or the age/sex of the patient indicates the medical test is fraudulent). The provider data or pre-established practice across providers (e.g., physician) may indicate that the presently requested medical tests requested by a different provider may be wasteful (e.g., redundant), an abuse of power, or fraudulent (e.g., intentionally redundant or not needed). The lab payer data or pre-established practice across lab payers (e.g., across various patients) may indicate that the presently requested medical tests may be wasteful (e.g., provide more information than needed and is not fully covered by the lab payer), an abuse of power (e.g., provide more information than needed but may be fully covered by the lab payer), or fraudulent (e.g., provide more information than needed but is known to be fully covered by the lab payer). Combinations of this data may be used to identify potential fraud, waste, and abuse.

When the lab clearinghouse device 120 determines that one or more of fraud, waste, and abuse may be present, the lab clearinghouse device 120 may generate a warning indication 528 and transmit the warning indication 530 to an appropriate party (e.g., a patient, provider, laboratory, lab payer, etc.). As shown in operation 528 and 530, the apparatus 200 includes means, such as processor 210; memory 220; input/output circuitry 240; communications circuitry 230; lab clearinghouse data store 300; fraud, waste, and abuse circuitry 400 (e.g., context determination circuitry 414, analytical engine 416, and/or communications interface 418); or the like, for generating a warning indication 528 and transmitting a warning indication 530. The warning indication may include a suggested revised lab request. For instance, the lab clearinghouse device 120 may determine that the performance of one or more medical tests requested in the lab request may be wasteful, then the lab clearinghouse device 120 may generate and transmit a warning indication to the lab request initiator indicating the defect in the lab request. In some embodiments, the warning indication may be transmitted to a patient indicating the defects in the lab request and requesting confirmation that the lab request should be approved. The warning indication may be sent to any of the patient (via a client device), provider 110A, lab payer 110B, laboratory 110C, or combinations thereof.

In some embodiments, the lab clearinghouse device 120 may determine that the ordering of the lab request may be an abuse of power, then the lab clearinghouse device 120 may generate and transmit a warning indication to the patient indicating the defect in the lab request.

In some embodiments, the lab clearinghouse device 120 may determine that the ordering of the lab request may be fraudulent, then the lab clearinghouse device 120 may generate and transmit a warning indication to the patient indicating the defect in the lab request.

As shown in FIG. 5, method (500) may include approving or denying the lab request (508). As shown in operation 508, the apparatus 200 includes means, such as processor 210; memory 220; input/output circuitry 240; communications circuitry 230; lab clearinghouse data store 300; fraud, waste, and abuse circuitry 400 (e.g., context determination circuitry 414, analytical engine 416, and/or communications interface 418); or the like, for approving or denying the lab request (508). In some embodiments, if it is determined that the lab request should be approved, a lab fee indication may be transmitted to one lab payer of the plurality of lab payers, lab instructions associated with the lab request may be generated, and lab instructions associated with the lab request may be transmitted to one laboratory of the plurality of medical laboratories for performance of the lab instructions.

As shown in operation 510, the apparatus 200 may include means, such as processor 210; memory 220; input/output circuitry 240; communications circuitry 230; lab clearinghouse data store 300; fraud, waste, and abuse circuitry 400 (e.g., context determination circuitry 414, analytical engine 416, and/or communications interface 418); or the like, for transmitting a lab fee indication to a lab payer (510). One or more lab payers 110B may receive the lab fee indication and a lab payment indication indicating that payment will be provided may be transmitted from one or more lab payers 110B. Lab payment may be transmitted at that time or at a later date. For example, in some embodiments, one or more insurance carriers may transmit a payment for the lab request and in some embodiments, a patient may be responsible for payment of part or all of the medical tests requested in the lab request. The patient may transmit a lab payment for the medical tests requested in the lab request. As shown in operation 512, the apparatus 200 may include means, such as processor 210; memory 220; input/output circuitry 240; communications circuitry 230; lab clearinghouse data store 300; fraud, waste, and abuse circuitry 400 (e.g., context determination circuitry 414, analytical engine 416, and/or communications interface 418); or the like, for receiving a lab payment from the lab payer (512).

As shown in operation 514, the apparatus 200 includes means, such as processor 210; memory 220; input/output circuitry 240; communications circuitry 230; lab clearinghouse data store 300; fraud, waste, and abuse circuitry 400 (e.g., context determination circuitry 414, analytical engine 416, and/or communications interface 418); or the like, for generating lab instructions to a laboratory (514) and for transmitting lab instructions to a laboratory (515). For instance, in some embodiments, the processor 210; memory 220; lab clearinghouse data store 300; fraud, waste, and abuse circuitry 400 (e.g., context determination circuitry 414, analytical engine 416, and/or communications interface 418); or the like, may generate lab instructions and the input/output circuitry 240 and/or communications circuitry 230 may transmit lab instructions to a laboratory.

The lab clearinghouse device 120 may generate lab instructions and transmit such instructions to one or more laboratories 110C. The lab instructions may specify certain medical tests to be performed, time and date of performance, conditions needed for performance of the medical tests (e.g., to avoid inaccurate testing, mishandling of specimens, or inconsistency across laboratories), and any other information that may enable the receiving laboratory 110C to perform the medical tests requested in the associated lab request. The lab instructions may be transmitted to a single laboratory 110C for performance of the one or more medical tests requested in the lab request. In some embodiments, the lab instructions may be transmitted to more than one laboratory 110C for performance of one or more medical tests requested in the lab request. The laboratory 110C to which lab instructions are transmitted may be determined by the lab request initiator. Each laboratory 110C may be instructed to perform a certain medical test or may be instructed that certain medical tests are needed and request confirmation of whether the medical tests can be performed. The lab clearinghouse device 120 may communicate with the laboratories 110C such that the medical tests requested in the lab request are performed.

As shown in operation 516, the apparatus 200 includes means, such as processor 210; memory 220; input/output circuitry 240; communications circuitry 230; lab clearinghouse data store 300; fraud, waste, and abuse circuitry 400 (e.g., context determination circuitry 414, analytical engine 416, and/or communications interface 418); or the like, for receiving a lab results indication (516). Once the medical tests are performed by the receiving laboratory 110C, the laboratory 110C may generate and transmit a lab results indication to the lab clearinghouse device 120. The lab results indication may indicate that lab results have been obtained and may list the lab results. The lab clearinghouse device 120 may then transmit the lab results indication with the lab results to one or more of the medical provider 110A and lab payer 110B associated with the lab request. In some embodiments, the lab clearinghouse device 120 may transmit the lab results indication with the lab results to the patient (via a client device) associated with the lab request using means such as input/output circuitry 240 and/or communications circuitry 230. The lab clearinghouse device 120 may store the lab results indication and the lab results in apparatus 200, such as in the lab clearinghouse data store 300.

The laboratory 110C may communicate solely with the lab clearinghouse device 120 to transmit lab results indications and lab results and receive payment for performance of the medical tests. As shown in operation 518, the apparatus 200 may include means, such as processor 210; memory 220; input/output circuitry 240; communications circuitry 230; lab clearinghouse data store 300; fraud, waste, and abuse circuitry 400 (e.g., context determination circuitry 414, analytical engine 416, and/or communications interface 418); or the like, for transmitting at least part of the lab payment (518). The laboratory 110C is more likely to receive payment (as payment has already been received by the lab clearinghouse device 120 prior to instructing performance of the medical tests, or payment has already been approved by the lab payer, even if payment has not yet been transmitted) and as a result, utilization of the lab clearinghouse system can eliminate the administrative and efficiency costs associated with following-up on payment for performance of the medical tests.

As shown in operation 520, the apparatus 200 includes means, such as processor 210; memory 220; input/output circuitry 240; communications circuitry 230; lab clearinghouse data store 300; fraud, waste, and abuse circuitry 400 (e.g., context determination circuitry 414, analytical engine 416, and/or communications interface 418); or the like, for transmitting lab results (520). Lab results may be transmitted to one or more of the lab payer 110B, provider 110A, and/or patient (via a client device).

In some embodiments, if it is determined that the lab request should be denied, a lab request denial may be transmitted to the lab request initiator. As shown in operation 522, the apparatus 200 includes means, such as processor 210; memory 220; input/output circuitry 240; communications circuitry 230; lab clearinghouse data store 300; fraud, waste, and abuse circuitry 400 (e.g., context determination circuitry 414, analytical engine 416, and/or communications interface 418); or the like, for transmitting a lab request denial to the lab request initiator (522).

The apparatus 200 may include means, such as processor 210; memory 220; input/output circuitry 240; communications circuitry 230; lab clearinghouse data store 300; fraud, waste, and abuse circuitry 400 (e.g., context determination circuitry 414, analytical engine 416, and/or communications interface 418); or the like, for generating a lab request denial. The lab request denial may indicate that the lab request needs to be revised and may include a suggested revised lab request. The lab request denial may deny the lab request without suggested revisions. The suggested revised lab request may be generated by the lab clearinghouse device 120 to overcome problems that were found with the original lab request. That is, the suggested revised lab request may include one or more medical tests to replace one or more medical tests requested in the original lab request. After determining whether fraud, waste, or abuse may be likely, the lab clearinghouse device 120 may determine that other medical tests would not be fraudulent, wasteful, or an abuse of discretion. The lab clearinghouse device has access to a variety of information (e.g., patient data, physician data, provider data, laboratory data, payer data, or combinations thereof) that may allow for providing suggested revised lab requests. The suggested revised lab request may include various information such as revised medical tests, revised patient data, etc.

After receiving the lab request denial, the lab request initiator (e.g., medical provider 110A) may generate and transmit the revised lab request to the lab clearinghouse device 120. As shown in method (500), the method may return to operation 502 where the revised lab request is received from the lab request initiator and evaluated for fraud, waste, and abuse. It will be appreciated that these operations are similar to the operations of receiving the lab request (502); determining whether fraud, waste, and abuse are likely (504); and approving or denying the lab request (508) as discussed above.

The revised lab request may include one or more medical tests to replace one or more medical tests requested in the original lab request. The revised lab request may include various information such as revised laboratories to perform the medical tests, revised medical tests, revised patient data, etc.

In some embodiments, the method (500) may include receiving the original lab request after transmitting the lab request denial. In some embodiments, instead of receiving a revised lab request, the original lab request may be resubmitted overriding the lab request denial. For instance, a provider, e.g., a physician, may determine that the original lab request should not have been denied and may resubmit the lab request without adjusting the content of the lab request. The method (500) may proceed directly to approving the original lab request (508) or not as discussed above.

Figure 6:
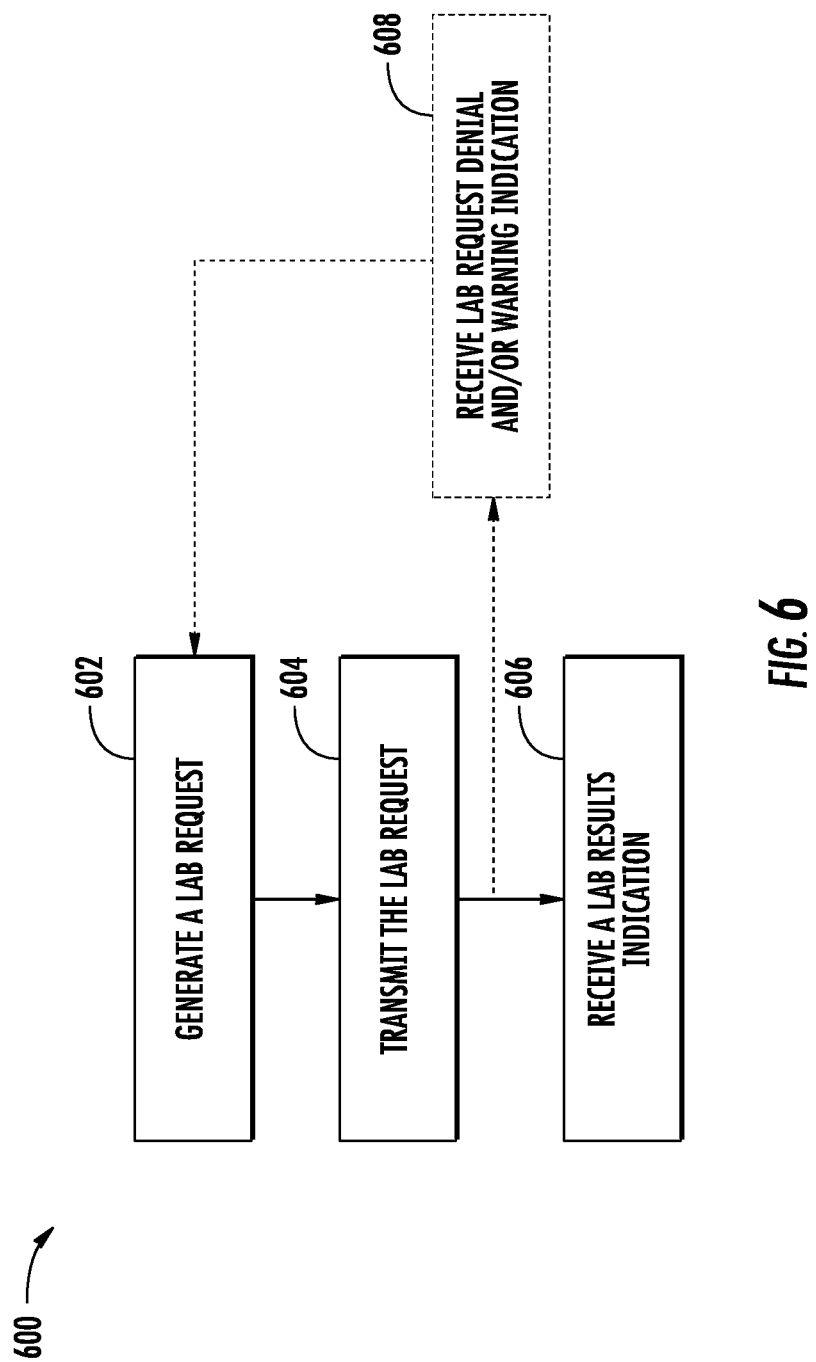
FIG. 6 illustrates a flow diagram of exemplary operations of a medical provider in accordance with some embodiments discussed herein.

FIG. 6 illustrates a flow diagram of exemplary operations of an example medical provider in accordance with some embodiments discussed herein. The operations illustrated in FIG. 6 may, for example, be performed by, with the assistance of, and/or under the control of an apparatus 200, as described above. In this regard, performance of the operations may invoke one or more of processor 210; memory 220; input/output circuitry 240; communications circuitry 230; fraud, waste, and abuse circuitry 400 (e.g., context determination circuitry 414, analytical engine 416, and/or communications interface 418); or the like. The medical provider 110A may include means, such as processor 210; memory 220; input/output circuitry 240; communications circuitry 230; fraud, waste, and abuse circuitry 400 (e.g., context determination circuitry 414, analytical engine 416, and/or communications interface 418); or the like for generating a lab request (602), transmitting a lab request to the lab clearinghouse device (604), and receiving a lab results indication (606). For instance, the input/output circuitry 240 and/or communications circuitry 230 may transmit a lab request (604) and receive a lab results indication (606). The processor 210, memory 220, lab clearinghouse circuitry 400, or the like may generate a lab request (602). In some embodiments, the medical provider 110A may include means, such as processor 210; memory 220; input/output circuitry 240; communications circuitry 230; fraud, waste, and abuse circuitry 400 (e.g., context determination circuitry 414, analytical engine 416, and/or communications interface 418); or the like for receiving a lab request denial and/or warning indication (608) and generating and transmitting a revised lab request or resubmit the lab request, such that the method (600) returns to operation 602. The medical provider may receive a lab request denial and/or warning indication and generate and transmit a revised lab request or resubmit the lab request.

Figure 7:
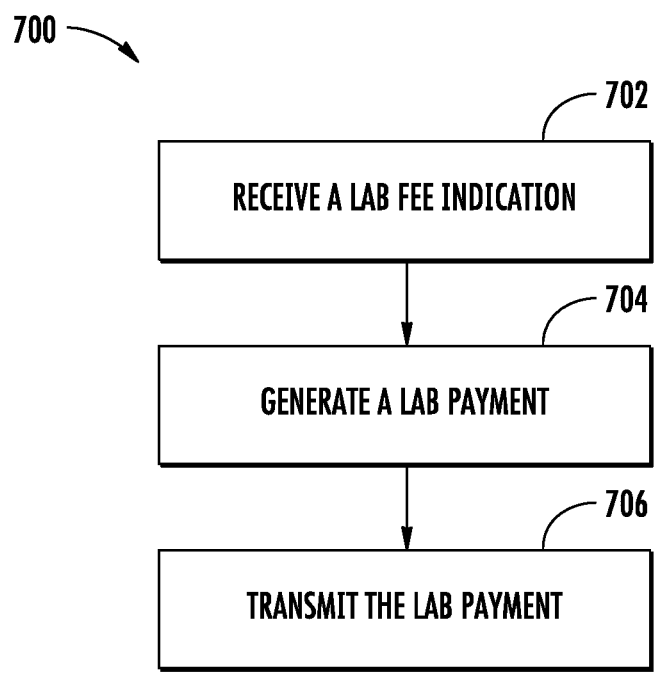
FIG. 7 illustrates a flow diagram of exemplary operations of a lab payer in accordance with some embodiments discussed herein.

FIG. 7 illustrates a flow diagram of exemplary operations of an example lab payer in accordance with some embodiments discussed herein. The operations illustrated in FIG. 7 may, for example, be performed by, with the assistance of, and/or under the control of an apparatus 200, as described above. In this regard, performance of the operations may invoke one or more of processor 210; memory 220; input/output circuitry 240; communications circuitry 230; fraud, waste, and abuse circuitry 400 (e.g., context determination circuitry 414, analytical engine 416, and/or communications interface 418); or the like, for receiving a lab fee indication (702), generating a lab payment (704), and transmitting a lab payment (706). For instance, the input/output circuitry 240 and/or communications circuitry 230 may receive a lab fee indication, the processor 210 and/or memory 220 may generate a lab payment, and the input/output circuitry 240 and/or communications circuitry 230 may transmit a lab payment. In some embodiments, the lab payer 110B may also include means, such as a processor 210; memory 220; input/output circuitry 240; communications circuitry 230; fraud, waste, and abuse circuitry 400 (e.g., context determination circuitry 414, analytical engine 416, and/or communications interface 418); or the like, for receiving a warning indication. For instance, the input/output circuitry 240 and/or communications circuitry 230 may receive a warning indication and the processor 210 and/or memory 220 may analyze the warning indication. Receiving a warning indication and analyzing the warning indication may occur prior to receiving a lab fee indication (702).

Figure 8:
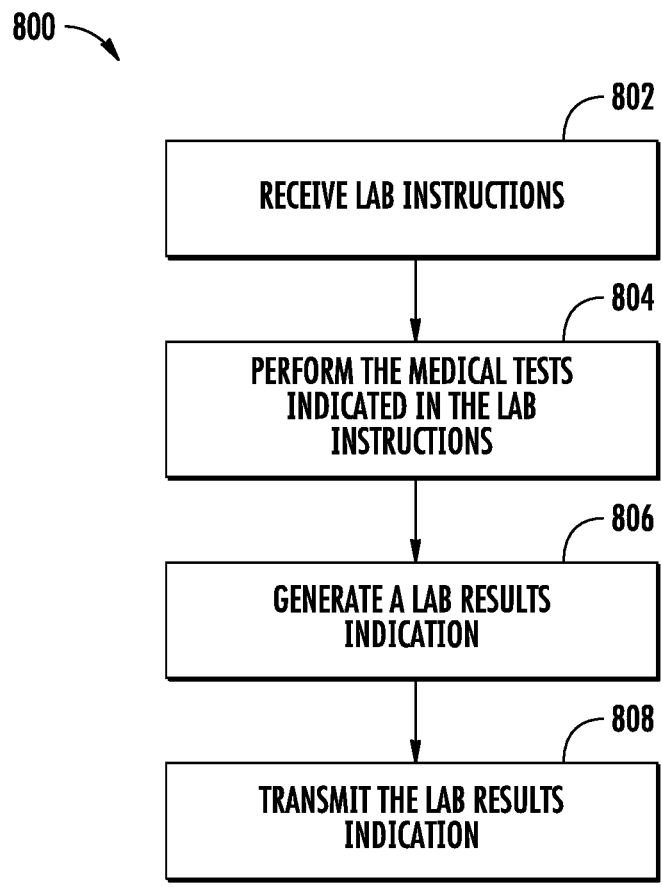
FIG. 8 illustrates a flow diagram of exemplary operations of a laboratory in accordance with some embodiments discussed herein.

FIG. 8 illustrates a flow diagram of exemplary operations of an example laboratory in accordance with some embodiments discussed herein. The operations illustrated in FIG. 7 may, for example, be performed by, with the assistance of, and/or under the control of an apparatus 200, as described above. In this regard, performance of the operations may invoke one or more of processor 210; memory 220; input/output circuitry 240; communications circuitry 230; fraud, waste, and abuse circuitry 400 (e.g., context determination circuitry 414, analytical engine 416, and/or communications interface 418); or the like. The laboratory 110C may include means, such as processor 210; memory 220; input/output circuitry 240; communications circuitry 230; fraud, waste, and abuse circuitry 400 (e.g., context determination circuitry 414, analytical engine 416, and/or communications interface 418); or the like, for receiving lab instructions (802), performing the medical tests indicated in the lab instructions (804), generating a lab results indication (806), and transmitting the lab results indication to the lab clearinghouse device (808). For instance, the input/output circuitry 240 and/or communications circuitry 230 may receive lab instructions, the processor 210 and/or memory 220 may perform the medical tests indicated in the lab instructions and/or generate a lab results indication, and the input/output circuitry 240 and/or communications circuitry 230 may transmit the lab results indication.

Provided herein are systems, methods, devices, and computer program products to reduce fraud, waste, and abuse where the lab clearinghouse device is designed to be the intermediary in transmissions between patients, providers (e.g., physicians, hospitals, etc.), lab payers, and laboratories, and as a result, the lab clearinghouse device has access to information, e.g., electronic medical records, from each of these entities. The lab clearinghouse device may provide real-time decision support integrations with the ordering provider (e.g., individual physician, physician group, hospital, clinic, etc.) workflow and may provide real-time analysis of a lab request based on information received from the provider, member (e.g., patient), lab payer, and laboratory to reduce fraud, waste, and abuse, and contract with the laboratory to perform the medical tests ordered in the lab request. The lab clearinghouse device can be used for learning and predictive analytics (e.g., prevalence of diseases based on specific genome markers) to determine whether fraud, waste, and abuse are likely. The lab clearinghouse device can be used to trim the volume of future lab work increasing the efficiency and effectiveness of the lab clearinghouse system compared to current practices. For instance, the lab clearinghouse device can determine whether fraud, waste, or abuse are likely by comparing the lab request to pre-established data concerning laboratories, providers, and lab payers. For instance, redundant or unnecessary labs can be avoided using historical patient data (e.g., by offering the results of a prior medical test instead of ordering a new medical test, warning the lab request initiator that the medical test was previously performed, or enabling the physician to see previously ordered medical tests for a specific patient). The lab clearinghouse system can thereby avoid waste, reducing costs for patients, providers, laboratories, and lab payers.

The lab clearinghouse device can establish pre-established practices associated with the lab request based on a series of lab requests specific to a provider of the plurality of medical providers. The series of lab requests may include lab requests associated with a plurality of different patients. Using the lab clearinghouse device, the frequency of a medical test ordered by one physician for a certain population of patients can be compared to other ordering physicians to identify—and thus avoid—abuse. The lab clearinghouse device can also avoid fraud (e.g., by matching the ordering physician or patient against a death file) using patient data as pre-established data.

In some embodiments, lab results may be transmitted to lab payers, medical providers, and patients (via client devices). The lab clearinghouse device may help reduce the effort associated with capturing supplemental data required for HEDIS and STARS and reduce the need to track down lab results from laboratories directly.

The lab clearinghouse device may allow for more accurate lab ordering by determining whether fraud, waste, and abuse are likely and modifying the lab request (e.g., using lab request denials and suggested revised lab requests), thereby reducing costs, system strain, and data processing for patients, laboratories (e.g., laboratories are more likely to be reimbursed for performance of the medical tests), lab payers, and medical providers. The lab clearinghouse device may have access to a variety of information concerning patients, laboratories, lab payers, and medical providers; can retrieve information from providers, lab payers, laboratories, and patients (via client devices); and is thereby able to more accurately evaluate and determine whether fraud, waste, and abuse are likely. For instance, the lab clearinghouse device may have access to both the lab request, specifying one or more medical tests to be performed, generate lab instructions, and receive and review lab results. The lab clearinghouse device may receive lab results thereby allowing the lab clearinghouse device to evaluate whether fraud, waste, and abuse are likely and use such information for determining whether fraud, waste, and abuse are likely with regards to future lab requests and further tailor the lab requests and lab instructions based on these determinations.

As the lab clearinghouse device analyzes the lab requests; transmits lab request denials and receives revised lab requests; has access to data concerning patients, laboratories, lab payers, and medical providers and can communicate with each of these parties (via a client device); and generates and transmits the lab instructions, the lab clearinghouse device may reduce issues associated with lab payers and laboratories not fully understanding the medical tests requested.

The lab clearinghouse device may determine whether fraud, waste, and abuse are likely prior to generation of lab instructions and performance of the medical tests requested in the lab request. This proactive system may reduce fraud, waste, and abuse, thereby reducing costs and increasing efficiency. Through the use of a lab clearinghouse system employing a lab clearinghouse device, all of the prior technical complexity can be avoided by with the single lab clearinghouse device designed to use pre-established data and determine whether fraud, waste, and abuse are likely prior to generation of lab instructions and performance of the lab requests.

Embodiments of the present invention have been described above with reference to block diagrams and flowchart illustrations of methods, devices, systems and computer program goods. It will be understood that each block of the circuit diagrams and process flowcharts, and combinations of blocks in the circuit diagrams and process flowcharts, respectively, can be implemented by various means including computer program instructions. These computer program instructions may be loaded onto a general purpose computer, special purpose computer, or other programmable data processing apparatus, such as processor 210, lab clearinghouse data store 300, and/or fraud, waste, and abuse circuitry 400 discussed above with reference to FIG. 2, to produce a machine, such that the computer program product includes the instructions which execute on the computer or other programmable data processing apparatus create a means for implementing the functions specified in the flowchart block or blocks.

These computer program instructions may also be stored in a computer-readable storage device (e.g., memory 220) that can direct a computer or other programmable data processing apparatus to function in a particular manner, such that the instructions stored in the computer-readable storage device produce an article of manufacture including computer-readable instructions for implementing the function discussed herein. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions discussed herein.

Accordingly, blocks of the block diagrams and flowchart illustrations support combinations of means for performing the specified functions, combinations of steps for performing the specified functions and program instruction means for performing the specified functions. It will also be understood that each block of the circuit diagrams and process flowcharts, and combinations of blocks in the circuit diagrams and process flowcharts, can be implemented by special purpose hardware-based computer systems that perform the specified functions or steps, or combinations of special purpose hardware and computer instructions.

Some embodiments of the present invention also use a second screen, as discussed herein. For instance, a first screen may be presented to a first user while a second screen may be presented to a second user of the lab clearinghouse system 100. The format of the display may appear differently to different users of the lab clearinghouse system 100. For instance, users may have particular preference for layouts or text fonts. The particular preferences may be considered when generating the communications and displays. The system may utilize any number of screens necessary for use of the lab clearinghouse system 100 in a meaningful way to each user of the system.

Many modifications and other embodiments of the inventions set forth herein will come to mind to one skilled in the art to which these embodiments of the invention pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An intermediary computing device in electronic communication with a plurality of medical provider computing devices, a plurality of lab payer computing devices, and a plurality of laboratory computing devices through one or more application programming interfaces (APIs), the intermediary computing device comprising a processor and a memory storing computer instructions that, when executed by the processor, cause the intermediary device to:
receive, via an API, an electronic message, wherein the electronic message comprises a lab request originating from a lab request initiator associated with a medical provider of a plurality of medical providers;

responsive to receiving the electronic message, automatically parse the electronic message to determine a context of the electronic message, wherein (a) the context of the electronic message is determined based at least in part on a sending user identifier in the electronic message, an attachment in the electronic message, or a determined topic of the electronic message, (b) the context of the electronic message is the lab request, (c) the lab request comprises first patient data, first medical provider data, and first lab data, (d) the first patient data comprises one or more of first patient name data, first patient preference data, first patient contact data, first patient gender data, first patient address data, first patient birthdate data, or first patient medical history data, (e) the first lab data comprises one or more of first lab location data or first lab pricing data, (f) the lab request comprises a request for one or more medical tests to be performed, (g) the lab request initiator operates a medical provider computing device of the plurality of medical provider computing devices, and (h) the lab request is parsed to identify the first patient data, the first medical provider data, and the first lab data;

programmatically determine, based at least in part on the first patient data, first medical provider data, and first lab data, that the lab request satisfies one or more pre-established data indicative of at least one of fraud, waste, or abuse;

responsive to determining that the lab request satisfies one or more pre-established data indicative of at least one of fraud, waste, or abuse, automatically generate and transmit an API-based notification to the medical provider computing device, wherein the API-based notification comprises a suggested revision to the lab request;

after automatically generating and transmitting an API-based notification to the medical provider computing device, receive second patient data, wherein the second patient data comprises one or more of second patient name data, second patient preference data, second patient contact data, second patient gender data, second patient address data, second patient birthdate data, or second patient medical history data;

programmatically determine, based at least in part on the first patient data, second patient data, first medical provider data, and first lab data, that the lab request does not satisfy the one or more pre-established data indicative of at least one of fraud, waste, or abuse; and responsive to determining that the lab request does not satisfy the one or more pre-established data indicative of at least one of fraud, waste, or abuse, approve the lab request based at least in part on the determination that the lab request does not satisfy the one or more pre-established data indicative of at least one of fraud, waste, or abuse, wherein approving the lab request comprises:
  generating lab instructions associated with the lab request after determining whether at least one of fraud, waste, or abuse in the lab request is likely, and
  transmitting, via an API, the lab instructions associated with the lab request to a laboratory computing device of the plurality of laboratory computing devices, wherein (a) the lab instructions comprise an indication to carry out the performance of the one or more corresponding medical tests, and (b) the lab instructions are displayed via an interface of the laboratory computing device of the plurality of laboratory computing devices.

2. The intermediary computing device of claim 1, wherein (a) the one or more pre-established data associated with the lab request comprise medical history of a patient associated with the lab request, and (b) the medical history of the patient comprises medical tests requested by a plurality of different providers.

3. The intermediary computing device of claim 1, wherein the one or more pre-established data associated with the lab request forms a pre-established practice regarding ordering of lab requests by the plurality of medical providers.

4. The intermediary computing device of claim 1, wherein the one or more pre-established data associated with the lab request comprise persistent patient data associated with the lab request.

5. The intermediary computing device of claim 1, wherein the computer instructions, when executed by the processor, cause a warning indication to be transmitted prior to generating lab instructions.

6. The intermediary computing device of claim 1, wherein the computer instructions, when executed by the processor, further cause the device to transmit a lab fee indication to one lab payer of the plurality of lab payers prior to generating lab instructions.

7. The intermediary computing The device of claim 1, wherein a lab request denial comprises a suggested revised lab request.

8. The intermediary computing device of claim 1, wherein the computer instructions, when executed by the processor, further cause the device to receive a lab payment.

9. The intermediary computing device of claim 8, wherein the computer instructions, when executed by the processor, further cause the device to receive lab results.

10. The intermediary computing device of claim 9, wherein the computer instructions, when executed by the processor, further cause the device to transmit the lab results to the lab request initiator.

11. A method of providing centralized management through an intermediary computing device in electronic communication with a plurality of medical provider computing devices, a plurality of lab payer computing devices, and a plurality of laboratory computing devices through one or more application programming interfaces (APIs), the intermediary computing, the method comprising:
  receiving, by an intermediary computing device via an API, an electronic message, wherein the electronic message comprises a lab request originating from a lab request initiator associated with a medical provider of a plurality of medical providers;
  responsive to receiving the electronic message, automatically parsing, by the intermediary computing device, the electronic message to determine a context of the electronic message, wherein (a) the context of the electronic message is determined based at least in part on a sending user identifier in the electronic message, an attachment in the electronic message, or a determined topic of the electronic message, (b) the context of the electronic message is the lab request (c) the lab request comprises first patient data, first medical provider data, and first lab data, (d) the first patient data comprises one or more of first patient name data, first patient preference data, first patient contact data, first patient gender data, first patient address data, first patient birthdate data, or first patient medical history data, (e) the first lab data comprises one or more of first lab location data or first lab pricing data, (f) the lab request comprises a request for one or more medical tests to be performed, (g) the lab request initiator operates a medical provider computing device of the plurality of medical provider computing devices, and (h) the lab request is parsed to identify the first patient data, the first medical provider data, and the first lab data;

programmatically determining, by an analytical engine and based at least in part on the first patient data, first medical provider data, and first lab data, that the lab request satisfies one or more pre-established data indicative of at least one of fraud, waste, or abuse;

responsive to determining that the lab request satisfies one or more pre-established data indicative of at least one of fraud, waste, or abuse, automatically generating and transmitting, by the intermediary computing device, an API-based notification to the medical provider computing device, wherein the API-based notification comprises a suggested revision to the lab request;

after automatically generating and transmitting an API-based notification to the medical provider computing device, receiving, by the intermediary computing device, second patient data, wherein the second patient data comprises one or more of second patient name data, second patient preference data, second patient contact data, second patient gender data, second patient address data, second patient birthdate data, or second patient medical history data;

programmatically determining, by the intermediary computing device and based at least in part on the first patient data, second patient data, first medical provider data, and first lab data, that the lab request does not satisfy the one or more pre-established data indicative of at least one of fraud, waste, or abuse; and responsive to determining that the lab request does not satisfy the one or more pre-established data indicative of at least one of fraud, waste, or abuse, approving, by the intermediary computing device, the lab request based at least in part on the determination that the lab request does not satisfy the one or more pre-established data indicative of at least one of fraud, waste, or abuse, wherein approving the lab request comprises:

generating lab instructions associated with the lab request after determining whether at least one of fraud, waste, or abuse in the lab request is likely, and transmitting, via an API, the lab instructions associated with the lab request to a laboratory computing device of the plurality of laboratory computing devices, wherein (a) the lab instructions comprise an indication to carry out the performance of the one or more corresponding medical tests, and (b) the lab instructions are displayed via an interface of the laboratory computing device of the plurality of laboratory computing devices.

12. The method of claim 11, wherein (a) the one or more pre-established data associated with the lab request comprise medical history of a patient associated with the lab request, and (b) the medical history of the patient comprises medical tests requested by a plurality of different providers.

13. The method of claim 11, wherein the one or more pre-established data associated with the lab request forms a pre-established practice regarding ordering of lab requests by the plurality of medical providers.

14. The method of claim 11 further comprising generating and transmitting, by the communications interface, a warning indication to a patient device.

15. The method of claim 11, wherein a lab request denial comprises a suggested revised lab request.

16. A computer program product is provided comprising a non-transitory computer readable medium having computer program instructions stored therein, said computer program instructions when executed by a processor of an intermediary computing device in electronic communication with a plurality of medical provider computing devices, a plurality of lab payer computing devices, and a plurality of laboratory computing devices through one or more application programming interfaces (APIs), to cause the computer program product to:

receive, via an API, an electronic message, wherein the electronic message comprises a lab request originating from a lab request initiator associated with a medical provider of a plurality of medical providers;

responsive to receiving the electronic message, automatically parse the electronic message to determine a context of the electronic message, wherein (a) the context of the electronic message is determined based at least in part on a sending user identifier in the electronic message, an attachment in the electronic message, or a determined topic of the electronic message, (b) the context of the electronic message is the lab request (c) the lab request comprises first patient data, first medical provider data, and first lab data, (d) the first patient data comprises one or more of first patient name data, first patient preference data, first patient contact data, first patient gender data, first patient address data, first patient birthdate data, or first patient medical history data, (e) the first lab data comprises one or more of first lab location data or first lab pricing data, (f) the lab request comprises a request for one or more medical tests to be performed, (g) the lab request initiator operates a medical provider computing device of the plurality of medical provider computing devices, and (h) the lab request is parsed to identify the first patient data, the first medical provider data, and the first lab data;

programmatically determine, based at least in part on the first patient data, first medical provider data, and first lab data, that the lab request satisfies one or more pre-established data indicative of at least one of fraud, waste, or abuse;

responsive to determining that the lab request satisfies one or more pre-established data indicative of at least one of fraud, waste, or abuse, automatically generate and transmit an API-based notification to the medical provider computing device, wherein the API-based notification comprises a suggested revision to the lab request;

after automatically generate and transmit an API-based notification to the medical provider computing device, receiving, by the intermediary computing device, second patient data, wherein the second patient data comprises one or more of second patient name data, second patient preference data, second patient contact data, second patient gender data, second patient address data, second patient birthdate data, or second patient medical history data;

programmatically determine, based at least in part on the first patient data, second patient data, first medical provider data, and first lab data, that the lab request does not satisfy the one or more pre-established data indicative of at least one of fraud, waste, or abuse; and responsive to determining that the lab request does not satisfy the one or more pre-established data indicative of at least one of fraud, waste, or abuse, approve the lab request based at least in part on the determination that the lab request does not satisfy the one or more pre-established data indicative of at least one of fraud, waste, or abuse, wherein approving the lab request comprises:

generating lab instructions associated with the lab request after determining whether at least one of fraud, waste, or abuse in the lab request is likely, and transmitting, via an API, the lab instructions associated with the lab request to a laboratory computing device of the plurality of laboratory computing devices, wherein (a) the lab instructions comprise an indication to carry out the performance of the one or more corresponding medical tests, and (b) the lab instructions are displayed via an interface of the laboratory computing device of the plurality of laboratory computing devices.

\* \* \* \* \*